(12) United States Patent
Mays et al.

(10) Patent No.: US 11,351,202 B2
(45) Date of Patent: *Jun. 7, 2022

(54) MAPC TREATMENT OF BRAIN INJURIES AND DISEASES

(71) Applicants: ATHERSYS, INC., Cleveland, OH (US); AUGUSTA UNIVERSITY RESEARCH INSTITUTE, INC., Augusta, GA (US)

(72) Inventors: Robert Mays, Cleveland Heights, OH (US); Robert J. Deans, Riverside, CA (US); David C. Hess, Martinez, GA (US); James E. Carroll, Augusta, GA (US); Cesar V. Borlongan, Augusta, GA (US)

(73) Assignees: ABT HOLDING COMPANY, Cleveland, OH (US); AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/849,181

(22) Filed: Dec. 20, 2017

(65) Prior Publication Data
US 2018/0296609 A1 Oct. 18, 2018

Related U.S. Application Data

(63) Continuation of application No. 12/161,830, filed as application No. PCT/US2007/001746 on Jan. 23, 2007, now Pat. No. 10,117,900, and a continuation-in-part of application No. 11/269,736, filed on Nov. 9, 2005, now Pat. No. 8,147,824.

(60) Provisional application No. 60/760,951, filed on Jan. 23, 2006.

(51) Int. Cl.
| | |
|---|---|
| A61K 35/28 | (2015.01) |
| A61K 35/50 | (2015.01) |
| A61K 35/545 | (2015.01) |
| A61K 38/13 | (2006.01) |
| A61K 45/06 | (2006.01) |
| C12N 5/074 | (2010.01) |
| A61K 31/4353 | (2006.01) |
| A61K 31/436 | (2006.01) |
| A61K 31/485 | (2006.01) |
| A61K 31/52 | (2006.01) |
| A61K 31/661 | (2006.01) |
| A61K 35/12 | (2015.01) |
| A61K 35/30 | (2015.01) |
| A61K 35/407 | (2015.01) |
| A61K 35/44 | (2015.01) |
| A61K 35/48 | (2015.01) |
| A61K 35/51 | (2015.01) |

(52) U.S. Cl.
CPC ........... *A61K 35/50* (2013.01); *A61K 31/436* (2013.01); *A61K 31/4353* (2013.01); *A61K 31/485* (2013.01); *A61K 31/52* (2013.01); *A61K 31/661* (2013.01); *A61K 35/12* (2013.01); *A61K 35/28* (2013.01); *A61K 35/30* (2013.01); *A61K 35/407* (2013.01); *A61K 35/44* (2013.01); *A61K 35/48* (2013.01); *A61K 35/51* (2013.01); *A61K 35/545* (2013.01); *A61K 38/13* (2013.01); *A61K 45/06* (2013.01); *C12N 5/0607* (2013.01)

(58) Field of Classification Search
CPC ........ A61K 35/28; A61K 35/50; A61K 35/51; A61K 35/545; A61K 35/30
See application file for complete search history.

(56) References Cited

U.S. PATENT DOCUMENTS

| | | |
|---|---|---|
| 4,353,888 A | 10/1982 | Sefton et al. |
| 4,744,933 A | 5/1988 | Rha et al. |
| 4,749,620 A | 6/1988 | Rha et al. |
| 4,814,274 A | 3/1989 | Shioya et al. |
| 5,084,350 A | 1/1992 | Chang et al. |
| 5,089,272 A | 2/1992 | Shioya et al. |
| 5,578,442 A | 11/1996 | Desai et al. |
| 5,639,275 A | 6/1997 | Baetge et al. |
| 5,676,943 A | 10/1997 | Baetge et al. |
| 6,245,781 B1 | 6/2001 | Upadhyay |
| 6,281,012 B1 | 8/2001 | McIntosh |
| 6,306,434 B1 | 10/2001 | Hong et al. |
| 6,328,960 B1 | 12/2001 | McIntosh |
| 6,355,239 B1 | 3/2002 | Bruder |
| 6,368,636 B1 | 4/2002 | McIntosh |
| 6,387,369 B1 | 5/2002 | Pittenger |
| 6,685,936 B2 | 2/2004 | McIntosh |
| 6,797,269 B2 | 9/2004 | Mosca |
| 6,875,430 B2 | 4/2005 | McIntosh et al. |
| 7,015,037 B1 | 3/2006 | Furcht et al. |
| 7,029,666 B2 | 4/2006 | Bruder |
| 7,510,873 B2 | 3/2009 | Mistry et al. |
| 7,514,074 B2 | 4/2009 | Pittenger |
| 8,147,824 B2 | 4/2012 | Maziarz |
| 11,000,546 B2 | 5/2021 | Deans et al. |

(Continued)

FOREIGN PATENT DOCUMENTS

| | | |
|---|---|---|
| EP | 0301777 A1 | 2/1989 |
| EP | 2241617 A1 | 10/2010 |

(Continued)

OTHER PUBLICATIONS

US 7,700,089 B2, 04/2010, Messina et al. (withdrawn)

(Continued)

*Primary Examiner* — Robert C Hayes
(74) *Attorney, Agent, or Firm* — Millen White Zelano and Branigan, PC; Larry Millstein; Jennifer J. Branigan

(57) ABSTRACT

The invention relates to the treatment of various injuries, disorders, dysfunctions, diseases, and the like of the brain with MAPCs, particularly in some aspects, to the treatment of the same resulting from hypoxia, including that caused by systemic hypoxia and that caused by insufficient blood supply. In some further particulars the invention relates, for example, to the treatment of hypoxic ischemic brain injury with MAPCs, in children for example, and to the treatment of cortical infarcts and stroke with MAPCs in adults, for example.

24 Claims, 11 Drawing Sheets

(56) References Cited

U.S. PATENT DOCUMENTS

| | | |
|---|---|---|
| 2002/0136723 A1 | 9/2002 | Feldman |
| 2003/0059414 A1 | 3/2003 | Ho et al. |
| 2004/0010745 A1 | 1/2004 | Lee et al. |
| 2004/0037811 A1 | 2/2004 | Penn et al. |
| 2004/0107453 A1 | 6/2004 | Furcht et al. |
| 2005/0233452 A1 | 10/2005 | Ho et al. |
| 2006/0008450 A1 | 1/2006 | Verfaillie |
| 2006/0263337 A1 | 11/2006 | Maziarz |
| 2007/0003530 A1 | 1/2007 | Pittenger |
| 2007/0122393 A1 | 5/2007 | McIntosh et al. |
| 2007/0134210 A1 | 6/2007 | Heidaran |
| 2008/0152624 A1 | 6/2008 | Paludan |
| 2008/0226595 A1 | 9/2008 | Edinger |
| 2008/0311084 A1 | 12/2008 | Veifaillie |
| 2008/0317740 A1 | 12/2008 | Blazar |
| 2009/0104163 A1 | 4/2009 | Deans |
| 2010/0310570 A1 | 12/2010 | Mays |
| 2012/0121545 A1 | 5/2012 | Kim et al. |
| 2012/0135043 A1 | 5/2012 | Maziarz |
| 2015/0118193 A1 | 4/2015 | Maziarz |

FOREIGN PATENT DOCUMENTS

| | | |
|---|---|---|
| EP | 2377542 A2 | 10/2011 |
| WO | 9947163 A2 | 9/1999 |
| WO | 2001011011 A1 | 2/2001 |
| WO | 2002064748 A1 | 8/2002 |
| WO | 2003025149 A1 | 3/2003 |
| WO | 2003059276 A1 | 7/2003 |
| WO | 2004069172 A1 | 8/2004 |
| WO | 2004099394 A1 | 11/2004 |
| WO | 2002056026 A1 | 6/2005 |
| WO | 2005113748 A2 | 12/2005 |
| WO | 2006121428 A1 | 11/2006 |
| WO | 2006121454 A1 | 11/2006 |
| WO | 07056578 A1 | 5/2007 |
| WO | 2007087293 A1 | 8/2007 |
| WO | 2008019148 A1 | 2/2008 |

OTHER PUBLICATIONS

Motooka Y, et al., Neurogenesis and axonal fiber sprouting following human multipotent adult progenitor cells (MAPC) transplantation in acutely ischemic rats,Neuroscience Meeting Planner [online], 2003≠, Presentation No. 42.2, [retrieved from the internet on Jul. 30, 2012]. <URL: http://www.sfn.org/absarchive/abstract.aspx>.
Myeloproliferative disorders. 2009. www.labtestsonline.org.au/understanding/conditions/myelopro—disorders-4.html. p. 1-2.
Nelson et al., "Stroke in newborn infants," Lancet Neurol., 2004, vol. 3, pp. 150-158.
Noonan, "Limitations on the Usefullness of Adult Stem Cells," Patent Doc., Biotech & Pharma Patent Law & News Blog, Mar. 2007, pp. 1-3.
Office Action for related Chinese Patent Application No. 200780010465.3 dated May 18, 2012.
Office Action for Related Chinese Patent Application No. 200780010390.9 dated Feb. 23, 2012.
Office Action for Related Japanese Patent Application No. 2008 552360 dated Aug. 7, 2012.
Orlic et al., "Transplanted Adult Bone Marrow Cells Repair Myocardial Infarets in Mice," Annals of the New York Academy of Sciences, 2001, pp. 221-230, New York Academy of Sciences.
Pincock, "Adult stem cell report questioned," The Scientist, Feb. 2007, pp. 1-4.
Pittenger, Science, 284: 143-147 (1999).
Prosper et al., "Phenotypic and Functional Characterization of Long-Term Culture—Initiating Cells Present in Peripheral Blood Progenitor Collections of Normal Donors treated with Granulocyte Colony-Stimulating Factor," Blood, Sep. 1996, pp. 2033-2042, vol. 88, No. 6, The American Society of Hematology.
Reyes, M. et al., "Characterization of multipotent adult progenitor cells, a subpopulation of Mesenchymal Stem Cells," Ann. NY Acad. Sci., 2001, vol. 938, pp. 231-235.
Ryan et al., "Mesenchymal stem cells avoid allogeneic rejection," Journal of Inflammation, Jul. 2005, pp. 1-11, vol. 2, No. 8, BioMed Central.
Sakai et al., "Fetal Cell Transplantation: A Comparison of Three Cell Types," The Journal of Thoracic and Cardiovascular Surgery, Oct. 1999, pp. 715-725, vol. 118, No. 4, Mosby, Inc.
Schwartz et al., "Multipotent adult progenitor cells from bone marrow differentiate into functional heatocyte-like cells," The Journal of Clinical Investigation, May 2002, pp. 1291-1302, vol. 109, No. 10, American Society of Sciences.
Serafini et al., "Hematopoietic reconstitution by multipotent adult progenitor cells: precursors to long-term hematopoietic stem cells," The Journal of Experimental Medicine, Jan. 2007, pp. 1-11; Correction to Serafini et al., J. Exp. Med., vol. 204, No. 1, Jan. 2007, pp. 129-139, The Rockefeller University Press.
Sigurjonsson et al., "Adult human hematopoietic stem cells produce neurons efficiently in the regenerating chicken embryo spinal cord," PNAS, Apr. 2005, pp. 5227-5232, vol. 102, No. 14, The National Academy of Sciences of the USA.
Sohn et al., "Stem cell therapy for muscular dystrophy," Expert Opin. Biol. Ther., 2004, pp. 1-9, vol. 4, No. 1, Ashley Publications Ltd.
Tolar, J. et al., "Multipotent Adult Progenitor Cells (MAPCs) Improve Cardiac Function after Ischemic Injury," Blood, 2005.
Tomita et al., "Autologous Transplantation of Bone Marrow Cells Improves Damaged Heart Function," Circulation, 1999, pp. II-247-II-256, American Heart Association, Inc.; Supplement to Circulatino, Journal of the American Heart Association, 1998, vol. 100, No. 19.
Tse et al., "Suppression of Allogeneic T-cell Proliferation by Human Marrow Stomal Cells: Implications in Transplantation," Transplantation, Feb. 2003, pp. 389-397, vol. 75, No. 3, Lippincott Williams & Wilkins, Inc.
Urtizberea, "Therapies in Muscular Dystrophy: Current Concepts and Future Prospects," European Neurology, 2000, pp. 127-132, vol. 43, S. Karger AG.
Van't Hof, W. et al., "Direct Injection of allogeneic multipotent adult progenitor cells improves Cardiac Function after Myocardial Infarct.," Blood, 2005.
Verfaillie, "Letter to the Editor," International Society for Experimental Hermatology, 35 (2007) 860, p. 1, Elsevier.
Xu, L. et al., Intrastriatal transplantation of cryoplantation of cryopreserved human bone marrow-derived multipotent adult progenitor cells at seven days after experimental ischemic stroke exerts dose-dependent behavioral recovery, Experimental Neurology, 2005, vol. 193, No. 1, pp. 265.
Yasuhara et al., "Transplantation of Cryopreserved Human Bone Marrow-derived Multipotent Adult Progenitor Cells for Neonatal Hypoxic-Ischemic Injury: Targeting the Hippocampus," Reviews in the Neurosciences, 2006, pp. 215-225, vol. 17, No. 1-2, Freund & Pettman, U.K.
Zhao, Robert Chunhua et al. "Mechanisms of and perspectives on the mesenchymal stem cell in Immunotherapy." Journal of Laboratory and Clinical Medicine. May 23, 2008. No. 6827673289, p. 2-9.
Zuk. Adipose-Derived Stem Cells in Tissue Regeneration: A Review. ISRN Stem Cells 2013, Article ID 713959, p. 1-35.
Decision on Motions—USPTO, TTAB Interference No. 105,953 SGL, *Ho et al.* v. *Furcht et al*, dated Sep. 26, 2014.
First Redeclaration—USPTO, TTAB Interference No. 105,953 SGL, *Ho et al.* v. *Furcht et al*, dated Sep. 26, 2014.
Judgment—USPTO, TTAB Interference No. 105,953 SGL, *Ho et al.* v. *Furcht et al*, dated Sep. 26, 2014.
Aldous et al., "Flawed stem cell data withdrawn," New Scientist, Feb. 2007, pp. 1-2.
Aldous et al., "Fresh questions on stem cell findings," New Scientist, Mar. 2007, pp. 12-13, vol. 12.
Barker, D. J. et al., "Fetal origins of cardiovascular disease," Ann. Med., 1999, vol. 31, Suppl. 1, pp. 3-6.

(56) References Cited

OTHER PUBLICATIONS

Barry, Frank P., and J. Mary Murphy. "Mesenchymal stem cells: Clinical applications and biological characterization." The International Journal of Biochemistry & Cell Biology. 2004, 36, p. 568-584.
Bartholomew et al., "Mesenchymal stem cells suppress lymphocyte proliferation in vitro and prolong skin graft survival in vivo," Int'l Society for Experimental Hematology, 2002, pp. 42-48, vol. 30, Elsevier Science Inc.
Bone Marrow Transplantation and Peripheral Blood Stem Cell Transplantation. 2010. NCI Factsheet. National Cancer Institute. downloaded from www.cancer.gov/cancertopics/factsheet/Therapy/bone-marrow-transplant. p. 1-15.
Borlongan et al., "Elevated body swing test: a new behavioral parameter for rats with 6-Hydroxydopamine-Induced hemiparkinsonism," J. Neurosci., 1995, vol. 15, pp. 5372-5378.
Carroll, J. E. et al., "Intracerebral grafts of cryopreserved syngeneic and allogeneic rat bone marrow-derived multipotent adult progenitor cells promote behavioral recovery in neonatal rats exposed to hypoxic-ischemic injury," Experimental Neurology, 2005, vol. 193, No. 1, pp. 241.
Check, "Stem-cell paper corrected," Nature, 2007, p. 1, Nature Publishing Group.
Chi, "Adult stem cell figure retracted," The Scientist, Jun. 2007, pp. 1-5, Nature Publishing Group.
Cutler et al., "Peripheral Blood Stem Cells for Allogeneic Transplantation: A Review," Stem Cells, 2001, pp. 108-117, vol. 19, AlphaMed Press.
Database Biosis, No. XP002427848, PREV200600133636, Blood, Nov. 2005, pp. 390B-391B, vol. 106, No. 11, Part 2, The American Society of Hematology.
Di Nicola et al., "Human bone marrow stromal cells suppress T-lymphocyte proliferation induced by cellular or nonspecific mitogenic stimuli," Blood, 2002, pp. 3838-3843, vol. 99, No. 10, The American Society of Hematology.
Donovan et al., "The end of the beginning for pluripotent stem cells," Nature, Nov. 2001, pp. 92-97, vol. 414, Macmillan Magazines Ltd.
English language translation of Japanese Office Action dated Aug. 11, 2015 for corresponding JP Application No. 2013-150313.
Farag, "Chronic graft-versus-host disease: where do we go from here?," Bone Marrow Transplantation, 2004, pp. 569-577, vol. 33, Nature Publishing Group.
Frassoni et al., "Expanded mesenchymal stem cells (MSC), coinfused with HLA identical hemopoietic stem cell transplants, reduce acute and chronic graft ersus host disease: A matched pair analysis," Bone Marrow Transplantation, 2002, p. S2, vol. 29, No. Suppl.2, XP002424218, Abstract 75, Nature Publishing Group.
Game et al., "Rejection mechanisms in transplanatation," Wiener Klinische Wochenschrift, 2001, pp. 832-838, vol. 113/20-21.
Heinonen et al., "Reproductive risk factors, pregnancy characteristics and obstetric outcome in female doctors," BJOG, 2002, vol. 109, pp. 261-264.
Huang et al. Spheroid formation of mesenchymal stem cells on chitosan and chitosanhyaluronan membranes. Biomaterials 32 (2011) 6929e6945.
Hughes, "Cardiac stem cells," Journal of Pathology, 2002, pp. 468-478, vol. 197, John Wiley & Sons, Ltd.
International Search Report issued in corresponding International Application No. PCT/US2007/001747, dated Jul. 27, 2007, 5 pages.
Jackowski, British Journal of Neurosurgery 9: 303-317 (1995).
Japanese Office Action dated Aug. 11, 2015 for corresponding JP Application No. 2013-150313.
Jiang et al., "Multipotent progenitor cells can be isolated from postnatal murine bone marrow, muscle, and brain," Experimental Hematology, Apr. 2002, pp. 896-904 vol. 30, Elsevier Science Inc.
Jiang et al., "Pluripotency of mesenchymal stem cells drived from adult marrow," (Corrections and Amendments), Nature, Jun. 2007, pp. 879-880, vol. 447, Nature Publishing Group.
Jiang, Y. et al., "Pluripotency of mesenchymal stem cells derived from adult marrow," Nature, vol. 418, pp. 41-49, (2002).
Jiao et al., "Long-term correction of rat model of Parkinson's disease by gene therapy," Nature, Apr. 1993, pp. 450-453, vol. 362, Nature Publishing Group.
Kavacsovics-Bankowski, M. et al., Multipotent adult progenitor cells (MPAC) Are Immunopriviledged and demonstrate Immunosuppressive Properties on Activated T Cell Population, Blood, Nov. 16, 2005, vol. 16, No. 11.
Keene et al., "Phenotypic Expression of Transplanted Human Bone Marrow-Derived Multipotent Adult Stem Cells into the Rat CNS," ASNTR Platform Session Abstracts, Apr. 2000, pp. 439, 465, Academic Press.
Kessler et al., "Myoblast Cell Grafting Into Heart Muscle: Cellular Biology and Potential Applications," Annu. Rev. Physiol. 1999, pp. 219-242, vol. 61, Annual Reviews.
Klug et al., "Genetically Selected Cardiomyocytes from Differentiating Embryonic Stem Cells Form Stable Intracardiac Grafts," J. Clin Invest., Jul. 1996, pp. 216-224, vol. 98, No. 1, American Society for Clinical Investigation, Inc.
Kocher et al., "Neovacularization of ischemic myocardium by human bone-marrowderived angioblasts prevents cardiomyocyte apoptosis, reduces remodeling and improves cardiac function," Nature Medicine, Apr. 2001, pp. 430-436, vol. 7, No. 4, Nature Publishing Group.
Koh et al., "Differentiation and Long-Term Survival of C2C12 Myoblast Grafts in Heart," J. Clin. Invest., Sep. 1993, pp. 1548-1554, vol. 92, American Society for Clinical Investigation, Inc.
Kopen et al., "Marrow stromal cells migrate throughout forebrain and cerebellum, and they differentiate into astrocytes after injection into neonatal mouse brains," Cell Biology, Sep. 1999, pp. 10711-10716, vol. 96, Proc. Natl. Acad. Sci. USA.
Krause et al., "Multi-Organ, Multi-Lineage Engraftment by a Single Bone Marrow-Derived Stem Cell," Cell, May 2001, pp. 369-377, vol. 105, Cell Press.
Lagasse et al., "Purified hematopoietic stem cells can differentiate into hepatocytes invio," Nature Medicine, Nov. 2000, pp. 1229-1234, vol. 6, No. 11, Nature America Inc.
Le Blanc et al., "Mesenchymal Stem Cells Inhibit and Stimulate Mixed LymphocyteCultures and Mitogenic Responses Independently of the Major HistocompatibilityComplex," Scandinavian Journal of Immunology, 2003, pp. 11-20, vol. 57, Blackwell publishing.
Le Blanc et al., "Treatment of severe acute graft-versus-host disease with third party haploidentical mesenchymal stem cells," Research Letters, May 2004, pp. 1439-1441, vol. 363, The Lancet.
Le Blanc, "Immunomodulatory effects of fetal and adult mesenchymal stem cells," International Society for Cellular Therapy, Cythotherapy 2003, pp. 485-489, vol. 5, No. 6, Taylor & Francis healthsciences.
Lemer et al., "Stem cell study was flawed, U panel finds," Feb. 2007, pp. 1-4. [on-line].Retrieved from the Internet: StarTribune.com. [retrieved on Feb. 23, 2007].
Long et al. 2005. Neural Cell Differentiation In Vitro from Adult Human Bone Marrow Mesenchymal Stem Cells. Stem Cells and Development 14:65-69.
Maitra et al., "Human mesenchymal stem cells support unrelated donor hematopoietic stem cells and suppress T-cell activation," Bone Marrow Transplanation, 2004, pp. 597-604, vol. 33, Nature Publishing Group.
Menasche et al., "Myoblast transplanatation for heart failure," The Lancet, Jan. 2001, pp. 279-280, vol. 357, The Lancet Publishing Group.
Menasche, "Skeletal muscle satellite cell transplantation," Cardiovascular Research, 2003, pp. 351-357, vol. 58, Elsevier Science B.V.
Moriscot et al. 2005. Human Bone Marrow Mesenchymal Stem Cells Can Express Insulin and Key Transcription Factors of the Endocrine Pancreas Developmental Pathway upon Genetic and/or Microenvironmental Manipulation In Vitro. Stem Cells 200523:594-604.
Search Report in corresponding EP appl. No. 17200032 dated Jun. 1, 2018.

(56) References Cited

OTHER PUBLICATIONS

Ong, Shin-Yeu et al: "Hepatic Differentiation Potential of Commercially Available Human Mesenchymal Stem Cells" Tissue Engineering—vol. 12, No. 12, Oct. 2006 (pp. 3477-3485).
Jia Yanjie et al; Effects of Notch-1 signalling pathway on differentiation of marrow mesenchymal stem cells into neurons in vitro ;NeuroReport. 18(14):1443-1447, Sep. 2007.
Karaöz E; A comprehensive characterization study of human bone marrow mscs with an emphasis on molecular and ultrastructural properties: J Cell Physiol. May 2011;226(5):1367-82.
Tang Y: Transplantation of bone marrow-derived stem cells: a promising therapy for stroke.Cell Transplant. 2007;16(2):159-69.
Jiang, Wenqi, et al., Cancer Biotherapy, Guangzhou Science & Technology Press, Chapter 6 Stem Cell Therapy, Section 2 Mesenchymal Stem Cells, Apr. 1, 2006, China (With English Translation Attached). pp. 1-9, partial translation.
Liu, Bin, Editor, Histology and Embryology, 1st Ed., Chap. 5(IV) Blood and Hemopoiesis, Peking University Medical Press, May 2005, China. pp. 1-7, partial translation.
Pei, Xuetao, Editor, Stem Cell Biology, 1st Ed., 17.2.2 Mesenchymal Stem Cells (MSCs), Jul. 2003, China (With English Translation Attached). pages 1-17 partial translation.
Li, Jingyuan et al., Telomerase Activity of Human Bone Marrow Mesenchymal Stem Cells, J. Zhejiang Univ. (Med Sci) 2004 Nov. 2004, 33(6):481-485, China. pp. 1-5, English Abstract Only.
Office Action in corresponding CN appln. 201810210598.5 dated Dec. 23, 2020 (pp. 1-7) and Search report (pp. 1-4).
Izadpanah et al. 2006. Biologic Properties of Mesenchymal Stem Cells Derived From Bone Marrow and Adipose Tissue. Journal of Cellular Biochemistry 99:1285-1297.
Jorgensen et al., "Engineering mesenchymal stem cells for immunotherapy," Gene Therapy, 2003, pp. 928-931, vol. 10, Nature Publishing Group.
Kovacsovics-Bankowski et al., "MultiStem (™) (multipotent adult progenitor cells) are non-immunogenic and display immunosuppressive properties on activated T cells, " 12th Annual Meeting of the Intrn'l Society for Cellular Therapy, 20006, Vo. 8, No. Suppl. 1, XP08076051, Abstract 166, Taylor & Francis healthsciences.
Punzel et al., "The Myeloid-Lymphoid Initiating Cell (ML-IC) Assay Assesses the Fate of Multipotent Human Progenitors in Vitro," Blood, Jun. 1999, pp. 3750-3756, vol. 93, No. 11, The American Society of Hematology.
Reyes et al., "Purification and ex vivo expansion of postnatal human marrow mesodemal progenitor cells," Blood, Nov. 2001, pp. 2615-2625, vol. 98, No. 9, The American Society of Hematology.
Shankaran et al., "Whole-Body Hypothermia for neonates with hypoxic-Ischemic encephalopathy," N. Engl. J. Med., 2005, vol. 353, pp. 1574-1584.
Miller et al., "Ex Vivo Culture of CD34/Lin/DR Cells in Stroma-Derived Soluble Factors, Interleukin-3, and Macrophage Inflammatory Protein-1 Maintains Not Only Myeloid But Also Lymphoid Progenitors in a Novel Switch culture Assay," Blood, Jun. 1998, pp. 4516-4522, The American Society of Hematology.
Van Raemdonck, Dirk et al., (2013). "Machine perfusion in organ transplantation", Current Opinion in Organ Transplantation, 18(1), 24-33.
Liu, L. et al. Telmerase deficiency impairs differentiation of mesenchymal stem cells. Exp Cell Res, 294(1), 1-8. (Abst).
Examiniation report in corresponding New Zeland application 714064 dated Mar. 25, 2021 (pp. 1-8).

MAPC TREATMENT OF BRAIN INJURIES AND DISEASES

REFERENCE TO RELATED APPLICATIONS

This application is a continuation of Ser. No. 12/161,830 filed Aug. 24, 2010, which is a 371 of PCT/US07/001746 filed Jan. 23, 2007, which claims priority benefit of U.S. 60/760,951 filed Jan. 23, 2006, and this application is a continuation in part of U.S. Ser. No. 11/269,736 filed Nov. 9, 2005, all of which applications and publications are incorporated herein by reference in their entirety and of which full benefit of priority is claimed for the present application.

FIELD OF THE INVENTION

The field of the invention is treatment of brain injury, disorder, dysfunction, and disease using multipotent adult progenitor cells ("MAPCs"), in particular the treatment of hypoxic and ischemic brain injuries, including but not limited to Hypoxic-Ischemic Brain Injury and Stroke.

BACKGROUND OF THE INVENTION

Brain injuries, including brain diseases, are a major health problem both in the US and worldwide. Many brain injuries arise from hypoxia, including focal hypoxias, often caused by stenosis or blockage in the blood supply to the brain, and diffuse hypoxias, generally caused by constrictions in a subject's air supply. Focal hypoxias can lead to, for instance, cortical infarcts and stroke. Diffuse hypoxias can lead to hypoxic ischemic brain injury ("HI injury"). Cortical infarcts and stroke, as well as HI injury, are significant health concerns.

HI injury and its related outcomes affect a significant number of live births every year. Measuring the incidence and effects of ischemic and hypoxic brain injury in children is complex; but, the number of patients affected is large by any assessment, HI injury has an incidence as high as 1 in 4000 live births. See Nelson et al., *Lancet Neurol.* 3:150-158 (2004). Most of these infants survive with considerable cognitive and motor deficits. See Barker, *Ann. Med.* 31: Suppl 1:3-6 (1999). Neonatal encephalopathy due to all causes occurs in 1 to 6 of every 1000 births. See, for instance, the American College of Obstetricians and Gynecologists website: www.acog.org. The risk of intrapartum neonatal asphyxia is estimated at 2.5% of all live births. See Heinonen et al., *BJOG* 109: 261-264(2002). Out of this large number of infants, a lesser number experience HI encephalopathy significant enough to produce brain injury with associated motor and cognitive disability. Cerebral palsy, or chronic, non-progressive motor disability, affects 1 to 2 per 1000 individuals in the United States. About 6% of these patients have acquired their disability through birth injuries related to HI injury. See, for instance, the NINDS website at www.ninds.nih.gov.

The current overall clinical outcome of term infants with HI injury is poor. Of all term neonates that suffer a HI injury, 10% die and 30% are permanently neurologically impaired. See Volpe, NEUROLOGY OF THE NEWBORN, 4th Ed., W.B. Saunders, Philadelphia (2001). Statistics generated from the control group of the recently published Phase I hypothermia trial, Randomized Controlled Trial of Hypothermia for Hypoxic-Ischemic Encephalopathy in Term Infants, found even higher levels of mortality: 37% of included neonates died and 25% were neurologically impaired. See Shankaran et al., *N Engl J Med.* 353: 1574-1584 (2005).

Other than supportive care, therapy for HI injury is limited. Whole body hypothermia has been reported as safe and beneficial in a multicenter Phase I clinical trial in treatment of neonatal HI. However, the usefulness of the therapy appears limited to the period shortly after birth. See Shankaran (2005) cited above.

The lack of therapy, number of affected individuals, coupled with the costs necessary to facilitate care and rehabilitation for life, indicate that HI injury represents a current, significant, unmet medical need. Much the same applies to a variety of other conditions characterized by damage to brain tissue, particularly cortical brain tissue, such as that resulting from hypoxia, infarction, and other injuries and/or insults, such as, for example injuries that produce ischemia and/or necrosis, such as ischemia and/or necrosis resulting in and/or associated with HI brain injury, cerebral accident, and/or stroke. There is therefore a need for improved methods for the treatment of these and related and similar injuries, pathologies, and diseases.

The use of stem cells has attracted some interest for this purpose, and there have been some encouraging observations in this area. A variety of stem cells have been isolated and characterized in recent years. They range from those of highly restricted differentiation potential and limited ability to grow in culture to those with apparently unrestricted differentiation potential and unlimited ability to grow in culture. The former have generally been the easier to derive and can be obtained from a variety of adult tissues. The latter have had to be derived from germ cells and embryos, and are called embryonal stem ("ES") sells, embryonal germ ("EG") cells, and germ cells. The embryonal stem ("ES") cell has unlimited self-renewal and can differentiate into all tissue types. ES cells are derived from the inner cell mass of the blastocyst. Embryonal germ ("EG") cells are derived from primordial germ cells of a post-implantation embryo. Stem cells derived from adult tissue have been of limited value because they are immunogenic, have limited differentiation potential, and have limited ability to propagate in culture. ES, EG, and germ cells do not suffer from these disadvantages, but they have a marked propensity to form teratomas in allogeneic hosts, raising due concern for their use in medical treatments. For this reason, there is pessimism about their utility in clinical applications, despite their advantageously broad differentiation potential. Stem cells derived from embryos also are subject to ethical controversies that may impede their use in treating disease.

Some efforts to find an alternative to ES, EG, and germ cells have focused on cells derived from adult tissue. While adult stem cells have been identified in most tissues of mammals, their differentiation potential is restricted and considerably more narrow than that of ES, EG, and germ cells. Indeed many such cells can give rise only to one or a few differentiated cell types, and many others are restricted to a single embryonic lineage. For instance, hematopoietic stem cells can differentiate only to form cells of the hematopoietic lineage, neural stem cells differentiate into cells only of neuroectodermal origin, and mesenchymal stem cells ("MSCs") are limited to cells of mesenchymal origin, (mesodermal cell types). Accordingly, these types of stem cells are, inherently, limited in their therapeutic applicability.

Accordingly, there has been, a need for stem cells that can be used for treatment of cortical infarcts, HI injury, and other diseases that have the self-renewing and differentiation capacity of ES, EG, and germ cells but are not immunogenic; do not form teratomas when allografted or xenografted to a host; do not pose other safety issues associated with ES, EG, and germ cells; retain the other advantages of ES, EG, and germ cells; are easy to isolate from readily available sources, such as placenta, umbilical cord, umbilical cord blood, blood, and bone marrow; can be stored safely for extended periods; can be obtained easily and without risk to volunteers, donors or patients, and others giving consent; and do not entail the technical and logistical difficulties involved in obtaining and working with ES, EG, and germ cells.

A type of cell, called herein multipotent adult progenitor cells ("MAPCs"), has been isolated and characterized (see, for Instance, U.S. Pat. No. 7,015,037, which is herein incorporated by reference in its entirety). ("MAPCs" also have been referred to as "MASCs.") These cells provide many of the advantages of ES, EG, and gem cells without many of their drawbacks. For example, MAPCs are capable of indefinite culture without loss of their differentiation potential. They show efficient, long term engraftment and differentiation along multiple developmental lineages in NOD-SCID mice and do so without evidence of teratoma formation (often seen with ES, EG, and germ cells) (Reyes, M. and C. M. Verfaillie *Ann NY Acad Sci.* 938: 231-5 (2001)).

SUMMARY OF THE INVENTION

In some of its embodiments, therefore, the invention provides methods for treating a brain injury, dysfunction, disorder, or disease, by (a) administering to a subject suffering from a brain injury, dysfunction, disorder, and/or disease cells (MAPCs) that: (i) are not embryonic stem cells, not embryonic germ cells, and not germ cells; (ii) can differentiate into at least one cell type of each of at least two of the endodermal, ectodermal, and mesodermal embryonic lineages; (b) with or without adjunctive immunosuppressive treatment.

In embodiments the injury, dysfunction, disorder, and/or disease is an injury, dysfunction, disorder, and/or disease of the cerebrum. In embodiments it is a injury, dysfunction, disorder, and/or disease in and/or of the cerebral cortex. In embodiments, it is a injury, dysfunction, disorder, and/or disease in and/or of the hippocampus. In embodiments it is a injury, dysfunction, disorder and/or disease in and/or of the cortex of the brain (also referred to as the cortical region of the brain).

In embodiments in regard to each and all of the foregoing, among others, the injury, dysfunction, disorder, and/or disease is an injury, dysfunction, disorder, and/or disease associated with and/or caused by a lack of oxygen. In embodiments in this regard the injury, dysfunction, disorder, and/or disease is caused by hypoxia. In embodiments in this regard the hypoxia is focal. In embodiments in this regard the hypoxia is diffuse. In embodiments in this regard the disease is hypoxic ischemic brain injury.

In embodiments further in regard to the same, the injury, dysfunction, disorder, and/or disease is an injury, dysfunction, disorder, and/or disease associated with and/or caused by in sufficient blood supply. In embodiments in this regard the injury, dysfunction, disorder, and/or disease is caused by an arterial or venous stenosis or blockage, including hut not limited to a blockage caused by a thrombus or a embolus. In embodiments in this regard, the injury, dysfunction, disorder, and/or disease is associated with and/or caused by an infarction and/or ischemia. In embodiments in this regard the injury, dysfunction, disorder, and/or disease is associated with and/or caused by necrosis. In embodiments in this regard the infract is a cortical infarct. In embodiments in this regard the injury, dysfunction, disorder, and/or disease is stroke.

In embodiments of the invention the cells (MAPCs) are used alone. In embodiments the cells are used together with other therapeutic agents as primary therapeutic modalities. In embodiments the cells are used as the sole therapeutic agent. In some embodiments the cells are used together with one or more other therapeutic agents. In some embodiments the cells are used alone or with one or more other therapeutic agents in one or more primary therapeutic modalities. In some embodiments the cells are used alone or with one or more other therapeutic agents is one or more adjunctive therapeutic modalities. In some embodiments the cells are used alone or with one or more other therapeutic agents in one or more primary and in one or more adjunctive therapeutic modalities.

Subject matter of the invention in some aspects and embodiments is further set forth illustratively in the following numbered paragraphs. The paragraphs are illustrative and not limitative of the invention, and a full understanding of the invention may be obtained only by reading the entirety of the present disclosure, including all text, all figures, the abstract provided herewith and interpreting the subject matter therein illustratively described from the viewpoint and with the knowledge and experience of a person skilled in the arts pertinent thereto and to which the invention pertains.

The phrase "according to any of the foregoing or the following" recited in any given numbered paragraph means the subject matter of that paragraph individually in each possible combination with the subject matter of any one or more other numbered paragraphs. In this regard, the paragraphs explicitly support claims to all such combinations of the subject matter recited therein. In certain instances, where the subject matter of a numbered paragraph is excluded from combination with the subject matter of a different numbered paragraph, the exclusion is denoted by the phrase "according to any of the foregoing or the following except number(s)" wherein the number(s) identify the excluded paragraph(s).

1. A method of treating a brain injury and/or brain dysfunction, and/or brain disorder and/or brain disease in a subject, comprising: administering to a subject likely to suffer, suffering, or who has suffered from a brain injury and/or brain dysfunction, and/or brain disorder and/or brain disease by an effective route and in an effective amount to treat said brain injury and/or brain dysfunction, and/or brain disorder and/or brain disease, cells (MAPCs) that; are not embryonic stem cells, embryonic germ cells, or germ cells, and cars differentiate into at least one cell type of each of at least two of the endodermal, ectodermal, and mesodermal embryonic lineages.

2. A method according to any of the foregoing or the following, except 60-65, wherein said subject is not treated with an immunosuppressive therapy adjunctively to treatment with said cells.

3. A method according to any of the foregoing or the following, wherein the brain injury and/or brain dysfunction, and/or brain disorder and/or brain disease is caused by hypoxia.

4. A method according to any of the foregoing or the following, wherein fee brain injury and/or brain dysfunction, and/or brain disorder and/or brain disease is caused by an occlusion or a blockage of blood supply to the brain.

5. A method according to any of the foregoing or the following, wherein the brain injury and/or brain dysfunction, and/or brain disorder and/or brain disease is an infarction.

6. A method according to any of the foregoing or the following, wherein the brain injury and/or brain dysfunction, and/or brain disorder and/or brain disease is a cortical infarction.

7. A method according to any of the foregoing or the following, wherein the brain injury and/or brain dysfunction, and/or brain disorder and/or brain disease is a stroke.

8. A method according to any of the foregoing or the following, wherein the brain injury and/or brain dysfunction, and/or brain disorder and/or brain disease is hypoxic ischemic brain injury.

9. A method according to any of the foregoing or the following, wherein said cells are not immunogenic in said subject.

10. A method according to any of the foregoing or the following, wherein said cells can differentiate into at least one cell type of each of the endodermal, ectodermal, and mesodermal embryonic lineages.

11. A method according to any of the foregoing or the following, wherein said cells express telomerase.

12. A method according to any of the foregoing or the following, wherein said cells are positive for oct-3/4.

13. A method according to any of the foregoing or the following, wherein said cells have undergone at least 10 to 40 cell doublings in culture prior to their administration to the subject.

14. A method according to any of the foregoing or the following, wherein said cells are mammalian cells.

15. A method according to any of the foregoing or the following, wherein said cells are human, horse, cow, goat, sheep, pig, rat, or mouse cells.

16. A method according to any of the foregoing or the following, wherein said-cells are human, rat, or mouse cells.

17. A method according to any of the foregoing or the following, wherein said cells are human cells.

18. A method according to any of the foregoing or the following, wherein said cells are derived from cells isolated from any of placental tissue, umbilical cord tissue, umbilical cord blood, bone marrow, blood, spleen tissue, thymus tissue, spinal cord tissue, adipose tissue, and liver tissue.

19. A method according to any of the foregoing or the following, wherein said cells are derived from cells isolated from any of placental tissue, umbilical cord tissue, umbilical cord blood, hone marrow, blood, and spleen tissue.

20. A method according to any of the foregoing or the following, wherein said cells are derived from cells isolated from any of placental tissue, umbilical cord tissue, umbilical cord blood, bone marrow, or blood.

21. A method according to any of the foregoing or the following, wherein said cells are derived from cells isolated from any one or more of bone marrow or blood.

22. A method according to any of the foregoing or the following, wherein said ceils are allogeneic to the subject.

23. A method according to any of the foregoing or the following, wherein said cells are xenogeneic to the subject.

24. A method according to any of the foregoing or the following, wherein said cells are autologous to the subject.

25. A method according to any of the foregoing or the following wherein the subject is a mammal.

26. A method according to any of the foregoing or the following wherein the subject is a mammalian pet animal, a mammalian livestock animal, a mammalian research animal, or a non-human primate.

27. A method according to any of the foregoing or the following, wherein the subject is a human.

28. A method according to any of the foregoing or the following, wherein said cells are administered to the subject in one or more doses comprising $10^4$ to $10^8$ of said cells per kilogram of the subject's mass.

29. A method according to any of the foregoing or the following, wherein said cells are administered to the subject in one or more doses comprising $10^5$ to $10^7$ of said cells per kilogram of the subject's mass.

30. A method according to any of the foregoing or the following, wherein said cells are administered to the subject in one or more doses comprising $5\times10^6$ to $5\times10^7$ of said cells per kilogram of the subject's mass.

31. A method according to any of the foregoing or the following, wherein said cells are administered to the subject in one or more doses comprising $2\times10^7$ to $4\times10^7$ of said cells per kilogram of the subject's mass.

32. A method according to any of the foregoing or the following, wherein in addition to said cells, one or more factors are administered to said subject.

33. A method according to any of the foregoing or the following, wherein in addition to said cells, one or more growth factors, differentiation factors, signaling factors, and/or factors that increase horning are administered to said subject.

34. A method according to any of the foregoing or the following, wherein in addition to said cells, one or more cytokines are administered to said subject.

35. A method according to any of the foregoing or the following, wherein said cells are administered to a subject adjunctively to another treatment that is administered before, at the same time as, or alter said cells are administered.

36. A method according to any of the foregoing or the following, wherein further one or more antibiotic agents is administered to said subject.

37. A method according to any of the foregoing or the following, wherein further one or more anti-fungal agents is administered to said subject.

38. A method according to any of the foregoing or the following, wherein further one or more anti-viral agents is administered to said subject.

39. A method according to any of the foregoing or the following, wherein further any combination of two or more of antibiotic agents and/or anti-fungal agents and/or anti-viral agents is administered to said subject.

40. A method according to any of the foregoing or the following, wherein said cells are administered in a formulation comprising one or more other pharmaceutically active agents.

41. A method according to any of the foregoing or the following, wherein said cells are administered in a formulation comprising one or more antibiotic agents.

42. A method according to any of the foregoing or the following, wherein said cells are administered in a formulation comprising one or more antifungal agents.

43. A method according to any of the foregoing or the following, wherein said cells are administered in a formulation comprising one or more antiviral agents.

44. A method according to any of the foregoing or the following, wherein said cells are administered to the subject by a parenteral route.

45. A method according to any of the foregoing or the following, wherein said cells are administered to the subject by any one or more of the following parenteral routes: intravenous, intraarterial, intracardiac, intraspinal, intrathecal, intraosseous, intraarticular, intrasynovial, intracutaneous, intradermal, subcutaneous, and intramuscular injection.

46. A method according to any of the foregoing or the following, wherein said cells are administered by any one or more of the following parenteral routes: intravenous, intraarterial, intracutaneous, intradermal, subcutaneous, and intramuscular injection.

47. A method according to any of the foregoing or the following, wherein said cells are administered by any one or more of the following parenteral routes: intravenous, intraarterial, intracutaneous, subcutaneous, and intramuscular injection.

48. A method according to any of the foregoing or the following, wherein said cells are administered to the subject through a hypodermic needle by a syringe.

49. A method according to any of the foregoing or the following, wherein said cells are administered to the subject through a catheter.

50. A method according to any of the foregoing or the following, wherein said cells are administered by surgical implantation.

51. A method according to any of the foregoing or the following, wherein said cells are administered to the subject by implantation using an arthroscopic procedure.

52. A method according to a any of the foregoing or the following, wherein said cells are administered to the subject by stereotactic injection.

53. A method according to any of the foregoing or the following, wherein said cells are administered to the subject in or on a support.

54. A method according to any of the foregoing or the following, wherein said cells are administered to the subject in an encapsulated form.

55. A method according to any of the foregoing or the following, wherein said cells are formulated suitably for administration by any one or more of the following routes: oral, rectal, epicutaneous, ocular, nasal, and pulmonary.

56. A method according to any of the foregoing or the following, wherein said cells are administered to the subject in one dose.

57. A method according to any of the foregoing or the following, wherein said cells are administered to the subject in a series of two or more doses in succession.

58. A method according to any of the foregoing or the following, wherein said cells are administered in a single dose, in two doses, or in more than two doses, wherein the doses are the same or different, and they are administered with equal or with unequal intervals between them.

59. A method according to any of the foregoing or the following, wherein said cells are administered over a period of less than one day to one week, one week to one month, one month to one year, one year to two years, or longer than two years.

60. A method according to any of the foregoing or the following, except 2, wherein in addition to treatment with said cells, the subject has been, will be, or is being treated with one or more immunosuppressive agents.

61. A method according to any of the foregoing or the following, except 2, wherein in addition to treatment with said cells, fee subject has been, will be, or is being treated with one or more of a corticosteroid, cyclosporin A, a cyclosporin-like immunosuppressive agent, cyclophosphamide, antithymocyte globulin, azathioprine, rapamycin, FK-506, and a macrolide-like immunosuppressive agent other than FK-506, and an immunosuppressive monoclonal antibody agent (i.e., an immunosuppressive that is an immunosuppressive monoclonal antibody or is an agent comprising a monoclonal antibody, in whole or in one or more pasts, such as a chimeric protein comprising an Fc or a Ag binding site of a monoclonal antibody).

62. A method according to any of the foregoing or the following, except 2, wherein in addition to treatment with said cells, the subject has been, will be, or is being treated with one or more of a corticosteroid, cyclosporin A, azathioprine, rapamycin, cyclophosphamide, FK-506, or an immunosuppressive monoclonal antibody agent.

63. A method according to any of the foregoing or the following, except 2, wherein said cells are administered in a formulation comprising one or more other immunosuppressive agents.

64. A method according to any of the foregoing or the following, except 2, wherein said cells are administered in a formulation comprising one or more of a corticosteroid, cyclosporin A, a cyclosporin-like immunosuppressive agent, cyclophosphamide, antithymocyte globulin, azathioprine, rapamycin, FK-506, and a macrolide-like immunosuppressive agent other than FK-506, and an immunosuppressive monoclonal antibody agent.

65. A method according to any of the foregoing or the following, except 2, wherein said cells are administered in a formulation comprising one or more of a corticosteroid, cyclosporin A, azathioprine, cyclophosphamide, rapamycin, FK-506, and an immunosuppressive monoclonal antibody agent.

The asterisks indicate a significant difference between the control group and the MAPC experimental group (Repeated Measures of ANOVA, p<0.0001; Fisher's PLSD posthoc t-test, p's<0.0001).

Figure 5:
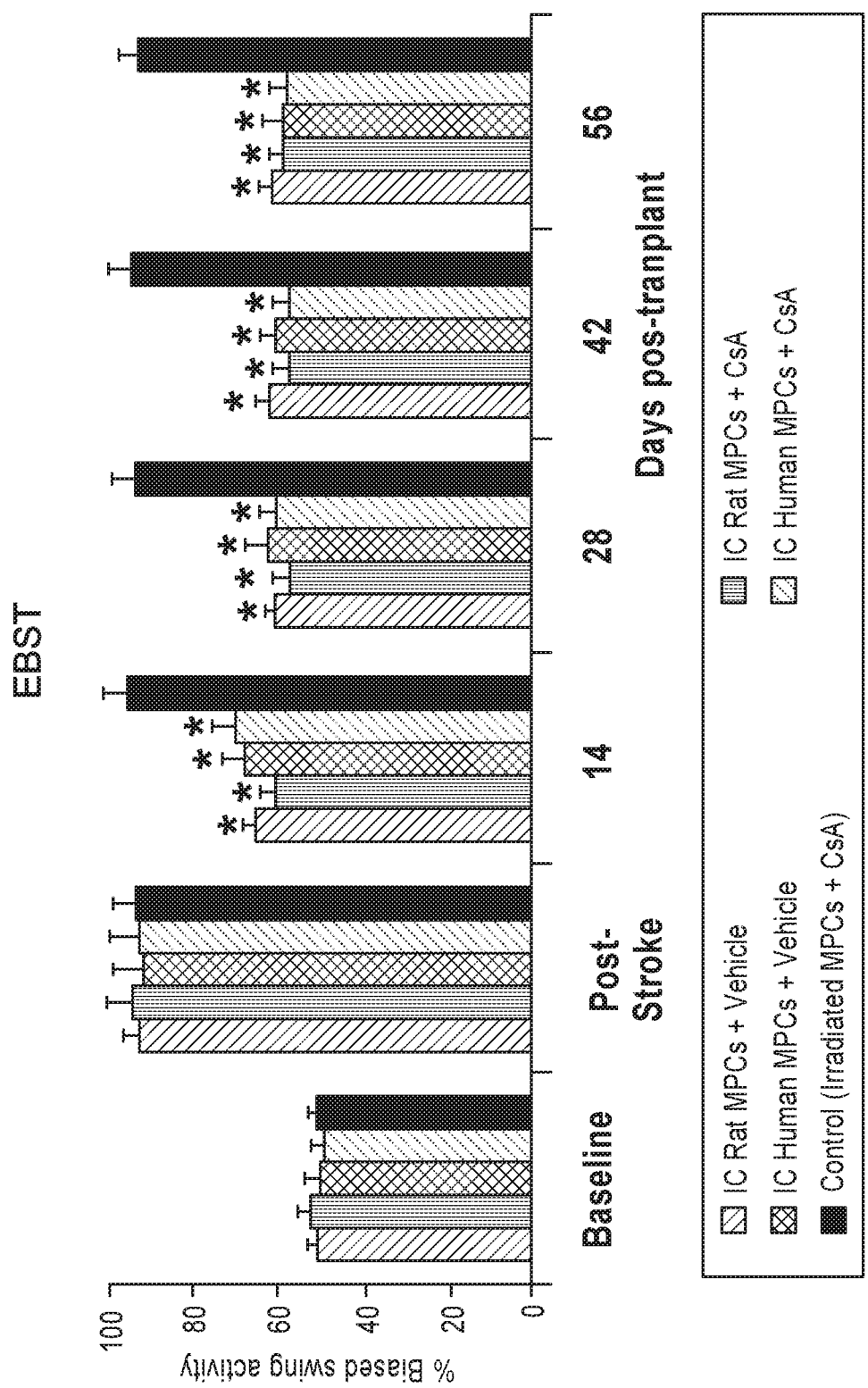

FIG. 5 is a graph showing that xenogeneic and allogeneic MAPC transplants promote sustained and statistically significant locomotor recovery following ischemic stroke in rats. Behavioral tests for locomotor functions were conducted on day 14, and on every 14th day thereafter for 56 days, as described in Example 10. Asterisks indicate statistical significance at p<0.0001 versus negative controls (non-viable irradiated MAPCs).

Figure 6:
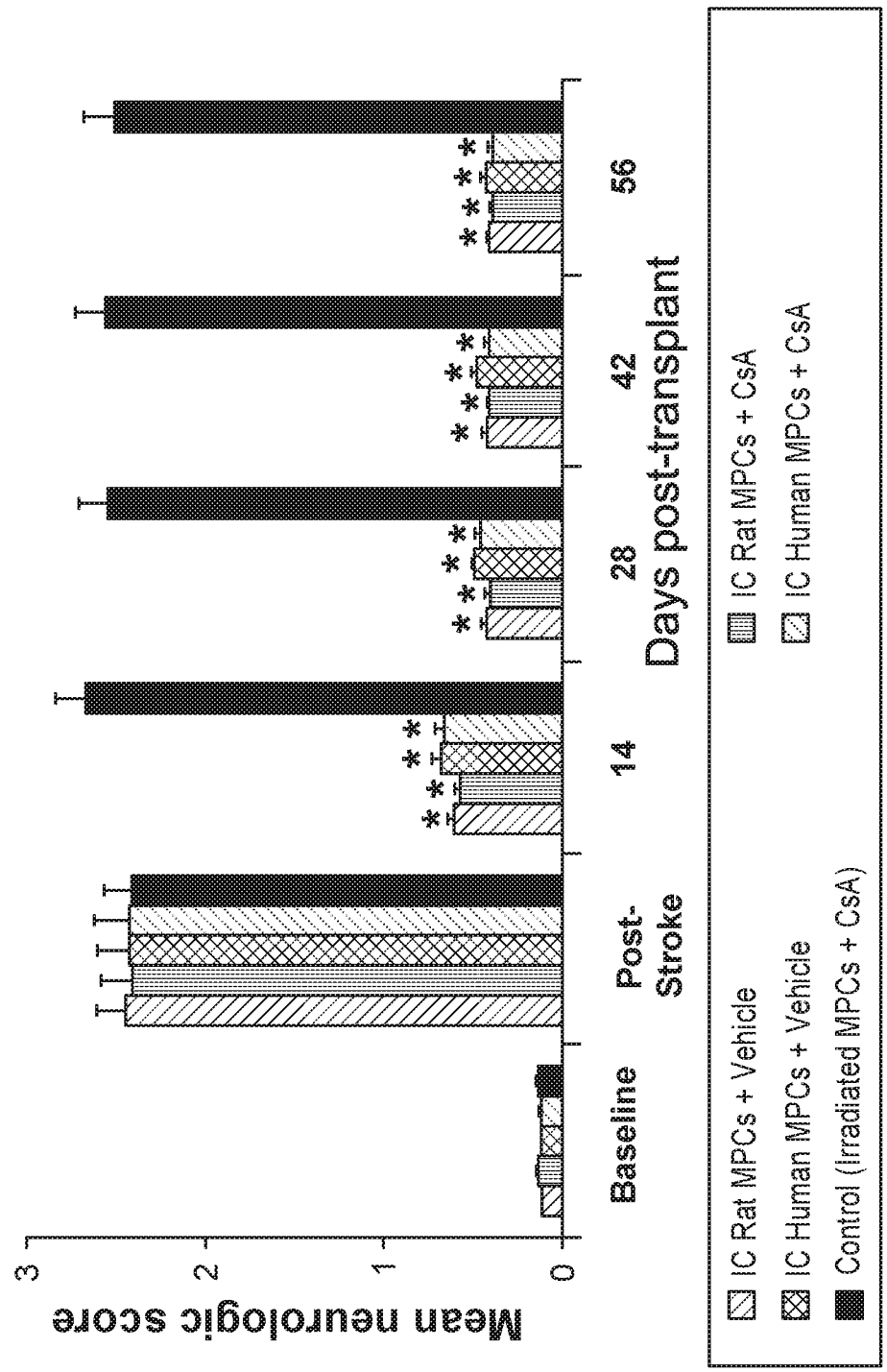

FIG. 6 is a graph showing that xenogeneic and allogeneic MAPC transplants promote sustained and statistically significant neurological recovery following ischemic stroke in rats. Behavioral tests for neurological functions were conducted on day 14 and on every 14th day thereafter for 56 days, as described in Example 10. Asterisks indicate statistical significance at p<0.0001 versus negative controls (non-viable irradiated MAPCs).

Figure 7:
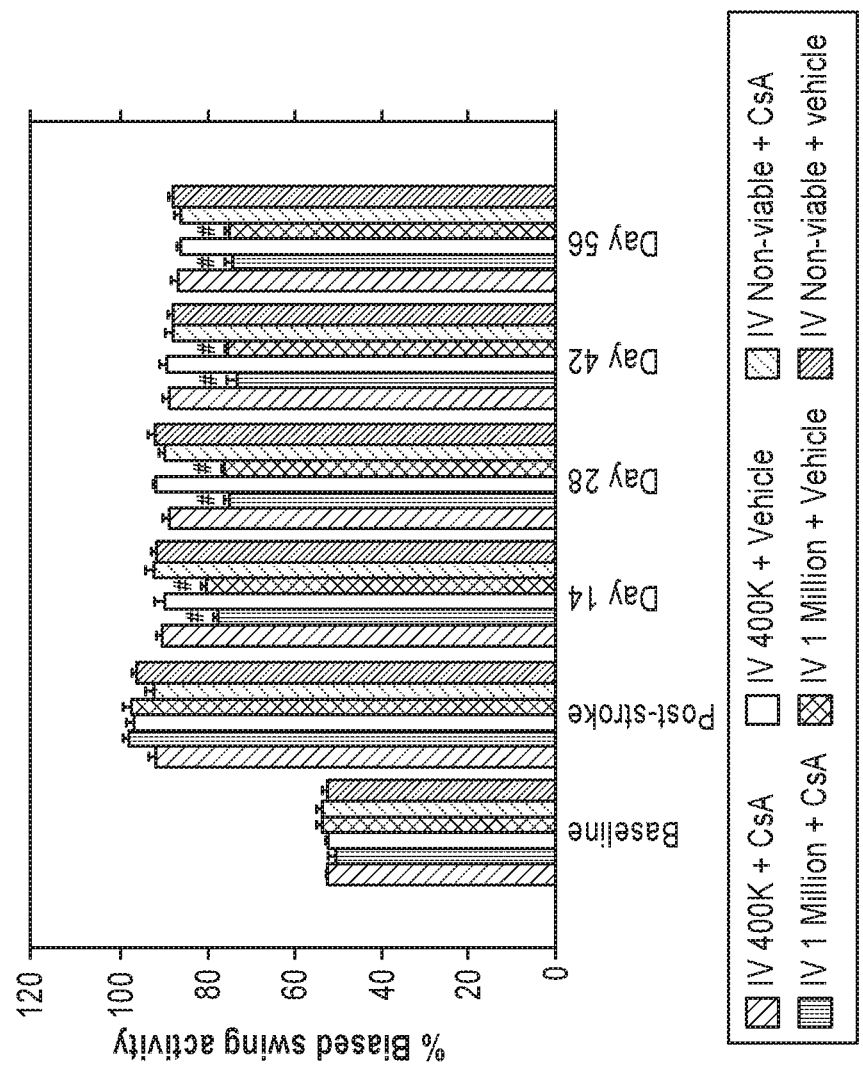

FIG. 7 is a graph showing a dose dependent improvement in locomotor function upon administration of xenogeneic MAPCs to rats with ischemic stroke, as described in Example 12. Behavioral tests for locomotor functions were conducted on day 14 and on every 14th day thereafter for 56 days. Asterisks indicate statistical significance at p<0.01 versus negative controls (non-viable Irradiated MAPCs).

Figure 8:
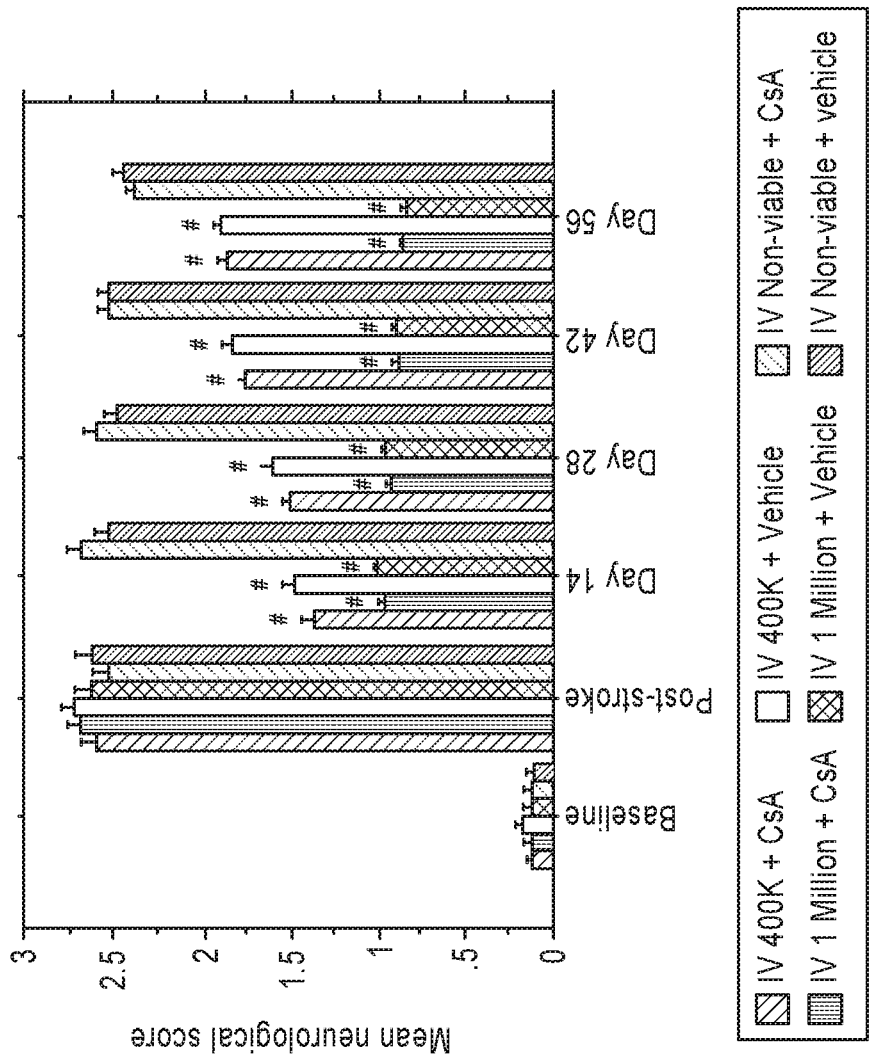

FIG. 8 is a graph, showing dose dependent improvements in neurological functions of ischemic stroke rats treated with xenogeneic MAPCs, as described in Example 12, Bederson tests for neurological functions were conducted on day 14 and every 14 days afterwards for 56 days. Asterisks indicate statistical significance at p<0.01 versus negative controls (non-viable irradiated MAPCs).

Figure 9:
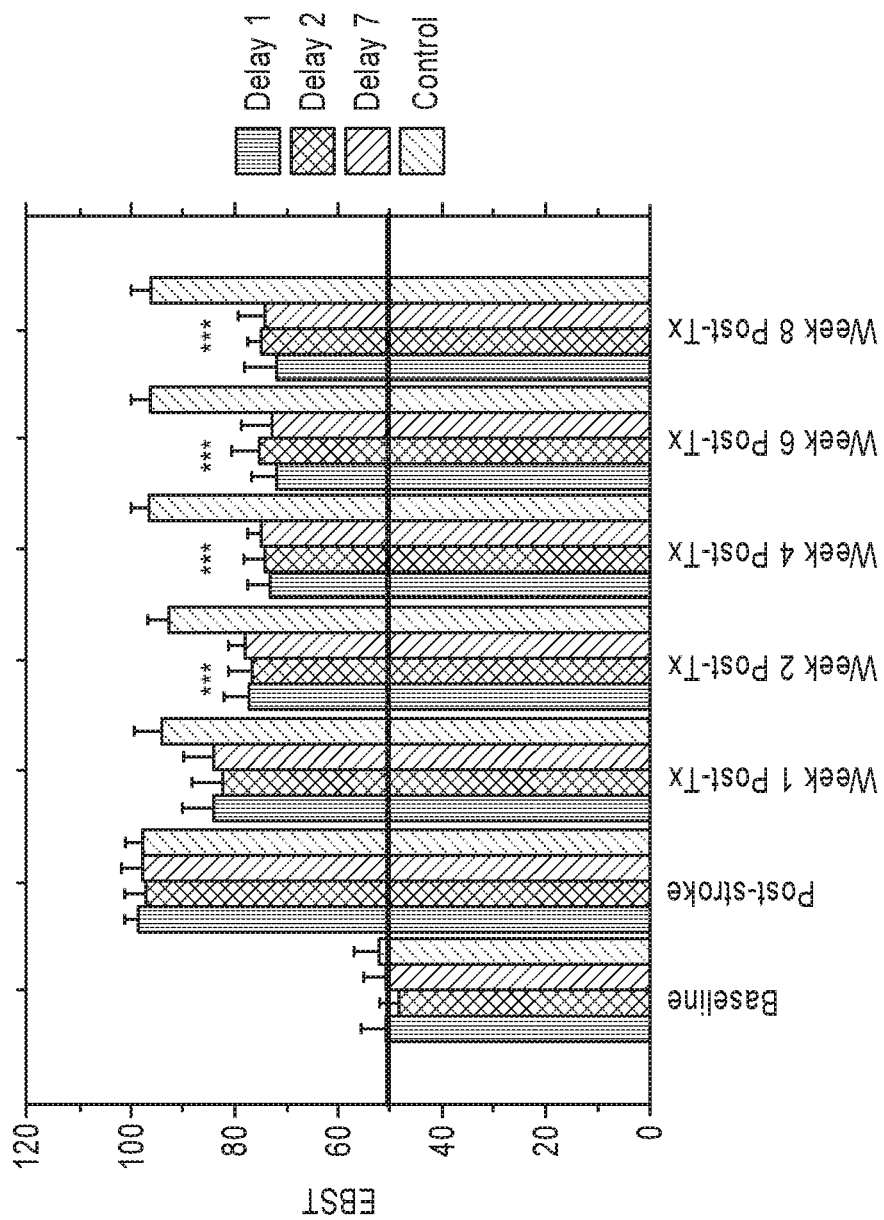

FIG. 9 is a graph showing dose dependent improvements in locomotor functions of ischemic stroke rats treated with xenogeneic MAPCs, as described in Example 14. EBST to measure locomotor function was conducted at one week after IV infusion and then once a week every week out to week 8 to demonstrate long term efficacy. Delay 1 indicates the group receiving cells one day after induction of ischemic injury, Delay 2 is the group that receives cells two days after injury, and Delay 7 the group which received cells seven days after ischemic injury. Asterisks indicate statistical significance at p<0.001 versus negative controls (non-viable irradiated MAPCs delivered at Day 7 after stroke).

Figure 10:
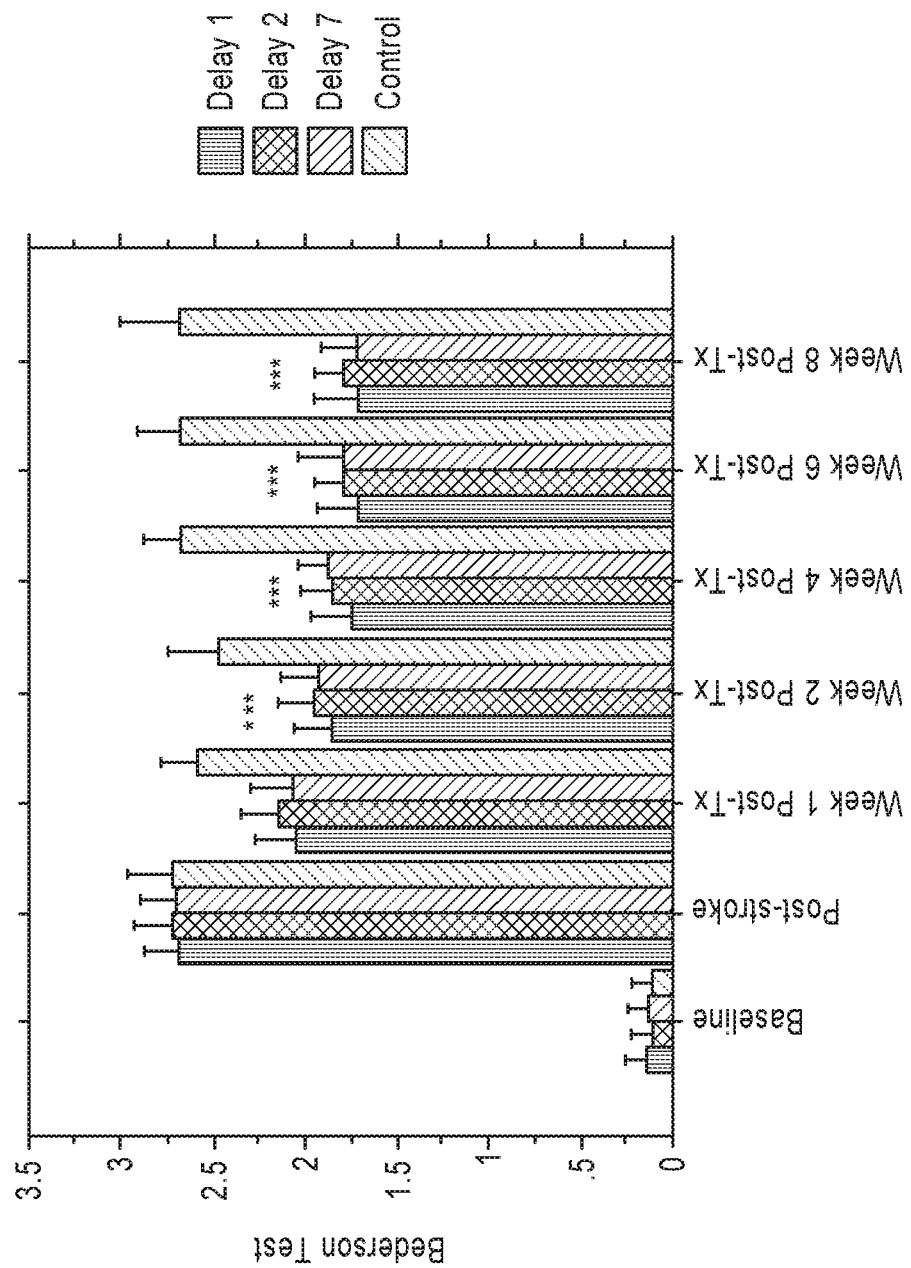

FIG. 10 is a graph showing dose dependent improvements in neurological function in ischemic stroke rats treated with xenogeneic MAPCs, as described in Example 14. Bederson Tests to measure neurological function were conducted at one week after IV infusion and then once a week every week out to week 8 to demonstrate long term efficacy. Delay 1 denotes the group receiving cells one day after induction of ischemic injury. Delay 2 denotes the group receiving cells two days after ischemic injury. Delay 7 denotes the group receiving cells seven days after ischemic injury. Asterisks indicate statistical significance at p<0.001 versus negative controls (non-viable irradiated MAPCs delivered at Day 7 after stroke).

Figure 11:
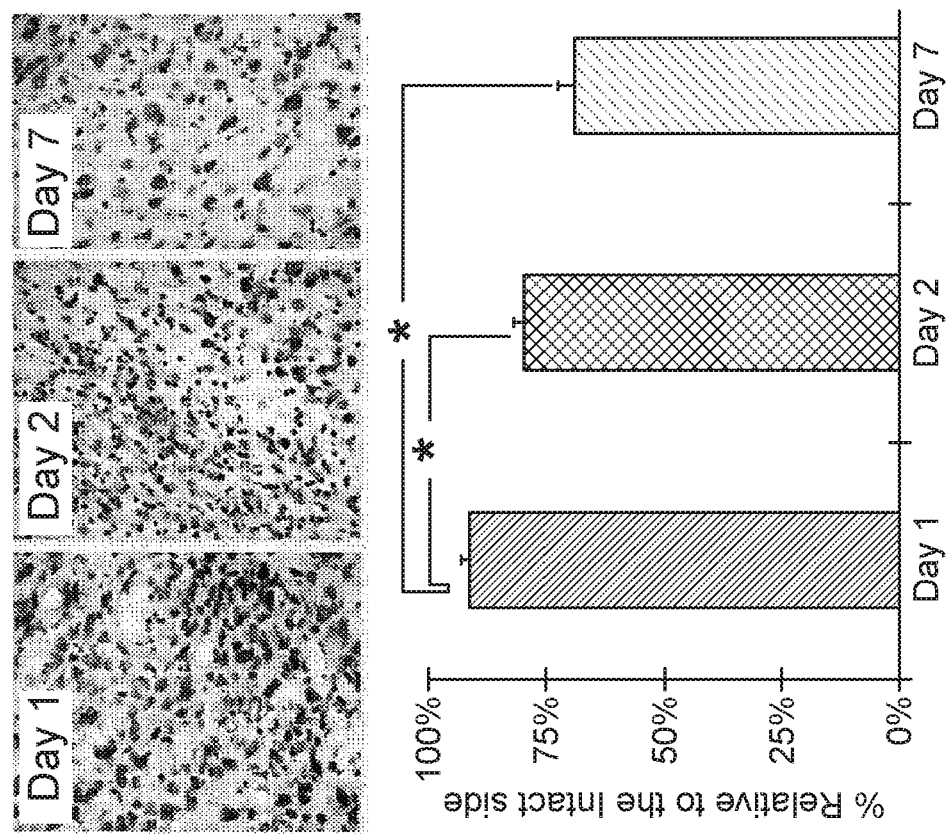

FIG. 11 is a graph and photos showing that the endogenous neuronal cell loss in ischemic stroke rats is reduced over time by IV infusion of MAPCs, as described in Example 16. Animals were sacrificed on Day 56 after the initiation of MAPC infusion. Brain section were prepared and Nissl stained for neuronal viability. Viability was determined in all the engrafted animals and neuronal viability was compared in animals receiving MAPCs at different times after injury. Viable cells per field were counted for each site of injury and for an uninjured site in the contralateral field on the same section, and the results were compared. The count for the uninjured contralateral site was set to 100%. The data, shown in the graph in FIG. 11, shows statistically significant protection of neurons in the penumbral region following MAPC transplantation Asterisks indicate statistical significance at p<0.05 versus other groups. Inserts above the graph show representative cross-sections of the injured sites.

GLOSSARY

Generally, terms and phrases are used herein in accordance with their art-established meanings. To avoid possibly ambiguity, nonetheless, the meanings of certain terms and phrases used herein are described below.

"A" or "an" means one or more; at least one.

"Adjunctive" means jointly, together with, in addition to, in conjunction with, and the like.

"Cerebral infarct," "cerebral infarction" refer to an ischemic condition of the cerebrum caused by an obstruction in the flow of blood to or through the cerebrum. Cerebral infarcts typically lead to necrosis of tissue that has been deprived of oxygen by loss of blood flow due to the obstruction. Cerebral infarcts often result in persistent focal neurological deficits.

"Cerebrovascular accidents" means the same as stroke.

"Cerebral ischemia" refers to the condition that occurs when blood flow to the cerebrum falls below the minimum required to maintain normal neurologic function. Cerebral ischemia is often caused by carotid artery stenosis, basilar artery stenosis, vertebral artery stenosis, and cerebral occlusive disease. It may also be caused by moyamoya disease and Takayasu's arteritis.

"Co-administer" can include simultaneous or sequential administration of two or more agents.

"Cortical" refers to the outer portion of an organ or a part of an organ or the like. For example the outer portion of the cerebrum is referred to as the cerebral cortex. The human cerebral cortex, is 2-4 mm (0.08-0.16 inches) thick and plays a central role in many complex brain functions. The surface of the human cerebral cortex is folded, and mare than two thirds of the cortical surface lies in the groove of the folds, called "sulci". The phylogenetically older part of the cerebral cortex is called the hippocampus. The more recently evolved portion is called the neo-cortex.

"Cortical infarct" refers to an infarct associated with a loss of blood supply to the cortex of the brain; typically an infarct associated with loss of blood supply to the cerebrum. Cortical infarct has much the same meaning as cerebral infarct.

"Cytokines" refer to cellular factors that induce or enhance cellular movement, snob as homing of MAPCs or other stem cells, progenitor cells, or differentiated cells. Cytokines may also stimulate such cells to divide.

"Deleterious" means, as used herein, harmful. By way of illustration, "deleterious immune response" means, as used herein, a harmful immune response, such as those that are lacking or are too weak, those that are too strong, and/or those that are misdirected. Also among deleterious immune responses are immune responses that interfere with medical treatment, including otherwise normal immune responses. Examples include immune responses involved in rejecting transplants and grafts, and the response of immunocompetent cells in transplants and grafts that cause graft versus host disease.

"Differentiation factors" refer to cellular factors, such as growth, factors, that induce lineage commitment.

"Dysfunction" means, as used herein, a disorder, disease, or deleterious effect of an otherwise normal process. By way of illustration, cortical infracts and lack of oxygen (hypoxia) can cause dysfunctions such as or leading to ischemic injury. Other dysfunctions also include, for instance, immune responses involved in rejecting transplants and grafts, and the response of immunocompetent cells in transplants and grafts that cause graft versus host disease, which generally then must be treated with immunosuppressive regimens.

"EC cells" refers to embryonic carcinoma cells.

"Effective amount" "effective dose" and the like generally mean an amount which provides the desired local or systemic effect. For example, an effective amount is an amount sufficient to effectuate a beneficial or desired clinical result. The effective amount can be provided all at once in a single administration or in fractional amounts that provide the effective amount in several administrations. For instance, an effective amount of MAPCs could be administered in one or more administrations and could include any preselected amount of cells. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. Thus, for instance, the skilled artisan in this art, such as a physician, based on the known properties of MAPCs as disclosed herein and in the art, together with a consideration of the foregoing factors, will be able to determine the effective amount of MAPCs for a given subject. As used herein, "effective dose" means the same as "effective amount."

In general the term effective in this context means sufficient to achieve a desirable outcome, which may by an improved prognosis and/or better patient status in some regard. Often it refers to amelioration or cure of an injury, dysfunction, disorder, or disease. In the case of brain injury, dysfunction, disorder, or disease, for instance, an effective dose may be one that achieves a desired neurological outcome, which may include decreasing cell damage over what would occur in the absence of treatment with the "effective" amount, halting altogether further cell damage, and/or reversing cell damage. "Effective" in this context also may be defined by a clinical outcome such as no further decline in neurological function and/or improvement in neurological function. Improvements in neurological function in this regard may be judged by any of a variety of tests and measures used for this purpose by care providers.

Much the same applies to effective doses and amounts as to other injuries, dysfunctions, disorders, and diseases.

"EG cells" refers to embryonal germ cells.

"Engraft" refers to the process of cellular contact and incorporation into an existing tissue of interest in vivo.

"Enriched population" means a relative increase in numbers of MAPCs relative to other cells or constituents in an initial population, such as an increase in numbers of MAPCs relative to one or more non-MAPC cell types in culture, such as primary culture, or in vivo.

"ES cells" refers to embryonal stem cells.

"Expansion" refers to the propagation of a cell or cells without differentiation.

"GVHD" refers to graft versus host disease, which means processes that occur primarily in an immunocompromised host when it is recognized as non-self by immunocompetent cells of a graft.

"HVG" refers to host versus graft response, which means processes which occur when a host rejects a graft. Typically, HVG is triggered when a graft is recognized as foreign, (non-self) by immunocompetent cells of the host.

"Hypoxia" refers to a lack of oxygen. In a neurological context, it refers to a reduction of oxygen to the brain, which may occur despite an adequate supply of blood. Hypoxia can arise from choking, strangling, suffocation, head trauma, carbon monoxide poisoning, cardiac arrest, and as a complication of general anesthesia, as well as from blood flow occlusion or blockage. Brain hypoxia leads to a cascade of events resulting in cell damage and cell death. Cerebral hypoxia/ischemia can be caused by a broad spectrum of diseases that affect the cardiovascular pumping system or the respiratory system. Cerebral hypoxia/ischemia is classified into four types: focal cerebral ischemia, global cerebral ischemia, diffuse cerebral hypoxia, and cerebral infarction.

Focal cerebral ischemia (FCI) is caused by a blood clot in the brain that reduces blood flow in the affected area. The severity of FCI varies, and it often causes irreversible injury to sensitive neurons. Global cerebral ischemia (GCI) is caused by ventricular fibrillation or cardiac asystole that terminates blood flow to the brain. Recovery from GCI that lasts longer than five to ten minutes is problematic. Longer GCI generally is fatal. Diffuse cerebral hypoxia (DCH) is caused by deficient blood oxygenation and typically results in mild to moderate hypoxemia. Pure DCH causes cerebral dysfunction but does not result in irreversible brain damage. It may be caused by pulmonary disease, altitude sickness, or severe anemia. Cerebral infarction (CI) results from a focal vascular occlusion in an area of the brain that causes necrosis.

"Infarct, "infarction" refers to an area of necrosis in a tissue resulting from ischemia (an obstruction in, blood flow) usually caused by a thrombus or embolus. It also refers to an obstruction in blood flow, resulting in ischemia, usually caused by a thrombus or embolus.

"Immunosuppression" refers to preventing, repressing, and/or reversing an immune response in a subject, such as for instance an immune response to a foreign antigen, such as allogeneic or xenogeneic cells or tissues. In some instances, for example, immunosuppressive treatment is required to suppress an immune response of a subject that would be adverse to a desired clinical outcome of treating the subject with a transplant of cells or of an organ.

"Ischemia" refers to a restriction in the supply of blood, typically because of vessel occlusion, resulting in dysfunction or damage to tissue that the occluded vessel supplies with oxygen. Ischemia also refers to an inadequate flow of blood to a part of a body caused by constriction or blockage of the Mood vessels. Ischemia in brain tissue initiates a cascade (referred to as the ischemic cascade) that results in release of proteolytic enzymes, reactive oxygen species, and other substances that may damage and ultimately kill brain tissue.

"Isolated" refers to a cell or cells which are not associated with one or more cells or one or more cellular components that are associated with the cell or cells in vivo or in primary culture.

"MAPC" is an acronym for "multipotent adult progenitor cell." It refers to a non-ES, non-EG, non-germ cell that can give rise to cell lineages of more than one germ layer, such as all three germ layers (I.e., endoderm, mesoderm, and ectoderm). MAPCs also have telomerase activity. They may be positive for oct-3/4 (e.g., human oct-3 A). They also may express one or more of rex-1, rox-1, sox-2, SSEA-4, and/or nanog. The term "adult" in MAPC is not restrictive. It only denotes that these cells are not ES, EG, or germ cells. Typically, as used herein, MAPC is singular and MAPCs is plural. MAPCs also have been referred to as multipotent adult stem cells (MASCs). See, for example, U.S. Pat. No. 7,015,037, which is herein incorporated by reference as to the methods disclosed therein for isolating and growing MAPCs/MASCs, which methods are merely exemplary and illustrative and in no way limitative of such methods useful in accordance in the invention.

"MASC," see MAPC.

"MNC" refers to mononuclear cells.

"Modality" means a type, approach, avenue, or method, such as, a therapeutic modality; i.e., a type of therapy.

"MSC" is an acronym for mesenchymal stem cells.

"Multipotent" with respect to MAPCs, refers to the ability to give rise to cell lineages of more than one germ layer, such as all three primitive germ layers (i.e., endoderm, mesoderm, and ectoderm) upon differentiation.

"Persistence" refers to the ability of cells to resist rejection and remain and/or increase in number over time (e.g., days, weeks, mouths, or years) in vivo.

"Primary culture" refers to the cell population obtained directly from an explant of material from an organism, before subculturing. Typically, primary cultures are established by (a) isolating tissue from an organism; (b) dissecting and/or disaggregating the tissue, and (c) allowing cells from the tissue to begin growing, either suspended in the media or, more typically, attached to a surface of the culture vessel. Primary cultures do not involve, and precede, subculturing the cells of the explant, such as by sub-dividing and diluting the cells and re-seeding them into fresh media and/or fresh culture vessels. Typically, a primary culture of attached cells is obtained by allowing cells to migrate out from a fragment of tissue adhering to a suitable substrate or by disaggregating the tissue mechanically or enzymatically to produce a suspension of cells, some of which then attach to the substrate.

"Progenitor" as used in multipotent adult progenitor cells (MAPCs) indicates that these cells can give rise to other cells such as further differentiated cells. The term is not limitative and does not limit these cells to a particular lineage.

"Self-renewal" refers to the ability to produce replicate daughter stem cells having differentiation potential that is identical to those from which they arose. A similar term used in this context is "proliferation."

"Stroke" is an acute neurological injury. It is caused in 80% of cases (referred to as ischemic stroke) by a disruption in the supply of blood to the brain that disturbs (an infarct), and typically interrupts, blood perfusion of the brain. The interruption may result from a disruption in arterial blood flow, but it can also result from a disruption in venous flow. The part of the brain where perfusion is disturbed does not receive adequate oxygen, causing cell damage and death. The result is a stroke.

Strokes may result in transient neurological impairment, permanent impairment or death. Impairment may be focal or generalized. Ischemic stroke is commonly classified as thrombotic stroke, embolic stroke, systemic hypoperfusion (Watershed or Border Zone stroke), or venous thrombosis. Thrombotic stoke is caused by a narrowing of an artery by a thrombus, usually involving an atherosclerotic plaque. Embolic stroke results from an arterial blockage by an embolus, most frequently a blood clot.

A "subject" is a vertebrate, such as a mammal, such as a human. Mammals include, hut are not limited to, humans, farm animals, sport animals, and pets. Subjects in need of treatment by methods of the present invention include those suffering from a disorder, dysfunction, or disease, such as a cortical infract and/or a hypoxic ischemic brain injury, or a side effect of the same, or a treatment thereof, that can benefit from administration of MAPCs either as a primary or an adjunctive treatment.

"Transplant" as used herein means to introduce into a subject, cells, tissues, or organs. The transplant can be derived from the subject, from culture, or from a non-subject source.

"Treat," "Treating," "treatment" and the like relate to the management and care of a patient, particularly with regard to combating a disorder or disease, including, but not limited to preventing, ameliorating, inhibiting, and/or curing a deficiency, dysfunction, disorder, or disease, or other process resulting with a deleterious effect, such as, for instance, combating, preventing, ameliorating, inhibiting and/or curing an injury, dysfunction, disorder, or disease. See also effective, effective amount, effective dose.

"Therapy" is synonymous with treatment.

DESCRIPTION OF THE INVENTION

As described herein, in accordance with certain aspects and embodiments of the invention, MAPCs can be used to treat brain injury, dysfunction, disorder, and/or disease, such as, but not limited to cortical infarcts and hypoxic ischemic brain injury with and without adjunctive immunosuppressive treatments.

Various embodiments of the invention provide methods for using MAPCs for precluding, preventing, combating, ameliorating, lessening, decreasing, minimizing, eliminating, and/or curing or the like an injury, dysfunction, disorder, and/or disease of the brain. In embodiments it is a injury, dysfunction, disorder, and/or disease in and/or of the cortex of the brain (also referred to as the cortical region of the brain). In embodiments it is an injury, dysfunction, disorder, and/or disease in and/or of the cerebrum. In embodiments it is a injury, dysfunction, disorder and/or disease in and/or of the cerebral cortex. In embodiments it is a injury, dysfunction, disorder, and/or disease in and/or of the hippocampus.

In embodiments in regard to each and all of the foregoing, among others, the injury, dysfunction, disorder, and/or disease is an injury, dysfunction, disorder, and/or disease associated with and/or caused by a lack of oxygen. In embodiments in this regard the injury, dysfunction, disorder, and/or disease is caused by hypoxia. In embodiments in this regard the hypoxia is focal. In embodiments in this regard the hypoxia is diffuse. In embodiments in this regard the disease is hypoxic ischemic brain injury.

In embodiments further in regard to the same, the injury, dysfunction, disorder, and/or disease is an injury, dysfunction, disorder, and/or disease associated with and/or caused by insufficient blood supply. In embodiments in this regard the injury, dysfunction, disorder, and/or disease is caused by an arterial or venous stenosis or blockage, including but not limited to a blockage caused by a thrombus or a embolus. In embodiments in this regard fee injury, dysfunction, disorder, and/or disease is associated with and/or caused by an infarction and/or ischemia. In embodiments in this regard the injury, dysfunction, disorder, and/or disease is associated with and/or caused by necrosis. In embodiments in this regard the infract is a cortical infarct. In embodiments in this regard the injury, dysfunction, disorder, and/or disease is stroke.

Embodiments provide methods for using MAPCs in this regard with adjunctive immunosuppressive treatment and/or therapy. Embodiments provide methods for using MAPCs in this regard without adjunctive immunosuppressive treatment.

In some of its embodiments, therefore, the invention provides cells that: (i) are not embryonic stem cells, not embryonic germ cells, and not germ cells; (ii) can differentiate into at least one cell type of each of at least two of the endodermal, ectodermal, and mesodermal embryonic lineages; and (iii) are effective for treating a brain injury and/or dysfunction and/or disorder and/or disease.

In embodiments the brain injury and/or dysfunction and/or disorder is caused by and/or associated with a lack of oxygen. In embodiments it is caused by or associated with hypoxia. In embodiments it is caused by or associated with a stenosis or blockage of blood supply. In embodiments it is or is associated with infarction and/or ischemia. In embodiments it is stroke. In embodiments it is hypoxia ischemic brain injury. In embodiments it is or is associated with a cortical infarct.

In embodiments of the invention the cells are used in this regard alone or together with other therapeutic agents and modalities as primary therapeutic modalities. In some embodiments of the invention the cells are used as the sole therapeutic agent or together with other therapeutic agents. In some embodiments of the invention the cells are used, alone or with other therapeutic agents or modalities, both in one or more primary therapeutic modalities and in one or more adjunctive therapeutic modalities.

MAPCs

Cells in accordance with the invention are described in greater detail herein and generally are referred to herein as "multipotent adult progenitor cells" and by the acronym "MAPC" (and "MAPCs" often used for the plural). It is to be appreciated that these cells are not ES, not EG, and not germ cells, and that they have the capacity to differentiate into cell types of at least two of the three primitive germ layer lineages (ectoderm, mesoderm, and endoderm), e.g., into cells of all three primitive lineages.

MAPCs can form the following cells, for example, among others, splanchnic mesodermal cells, muscle cells, bone cells, cartilage cells, endocrine cells, exocrine cells, endothelial cells, hair forming cells, teeth forming cells, visceral mesodermal cells, hematopoietic cells, stromal cells, marrow stromal cells, neuronal cells, neuroectodermal cells, epithelial cells, ocular cells, pancreatic cells, and hepatocyte-like cells, and cells of the same lineages, among many others. For example, among cells formed by MAPCs are osteoblasts, chondroblasts, adipocytes, skeletal muscle cells, skeletal myocytes, biliary epithelial cells, pancreatic acinary cells, mesangial cells, smooth muscle cells, cardiac muscle cells, cardiomyocytes, osteocytes, vascular tube forming cells, oligodendrocytes, neurons, including serotonergic, GABAergic, dopaminergic neurons, glial cells, microglial cells, pancreatic epithelial cells, gut epithelial cells, liver epithelial cells, skin epithelial cells, kidney epithelial cells, renal epithelial cells, pancreatic islet cells, fibroblasts, hepatocytes, and other cells of the same lineages as the foregoing, among many others.

MAPCs have telomerase activity necessary for self-renewal and to avoid replicative senescence. Generally they also express oct-3/4. Oct-3/4 (oct-3A in humans) is otherwise specific to ES, EG, and germ cells. It is considered to be a marker of undifferentiated cells that have broad differentiation abilities. Oct-3/4 also is generally thought to have a role in maintaining a cell in an undifferentiated state. Oct-4 (oct-3 in humans) is a transcription factor expressed in the pregastrulation embryo, early cleavage stage embryo, cells of the inner cell mass of the blastocyst, and embryonic carcinoma ("EC") cells (Nichols, J, et al. (1998) *Cell* 95: 379-91), and is down-regulated when cells are induced to differentiate. The oct-4 gene (oct-3 in humans) is transcribed into at least two splice variants in humans, oct-3 A and oct-3B. The oct-3B splice variant is found in many differentiated cells whereas fee oct-3A splice variant (also previously designated oct-3/4) is reported to be specific for the undifferentiated embryonic stem cell See Shimozaki et al. (2003)*Development* 130: 2505-12. Expression of oct-3/4 plays an important role in determining early steps in embryogenesis and differentiation. Oct-3/4, In combination with rox-1, causes transcriptional activation of the Zn-finger protein rex-1, which is also required for maintaining ES cells in an undifferentiated state (Rosfjord, E, and Rizzino, A. (1997) *Biochem Biophys Res Commun* 203: 1795-802; Ben-Shushan, B, et al. (1998) *Mol Cell Biol* 18: 1866-78).

MAPCs may also express other markers. Among these are rex-1, rox-1, and sox-2. Rex-1 is controlled by oct-3/4, which activates downstream expression of rex-1. Rox-1 and sox-2 are expressed in non-ES cells.

In some embodiments of the invention MAPCs are used together with one or more other agents and/or therapeutic modalities as the primary therapeutic modality. In some embodiments of the invention the cells are used as an adjunctive therapeutic modality, that is, as an adjunct to another, primary therapeutic modality. In some embodiments the cells are used as the sole active agent of an adjunctive therapeutic modality. In others the cells are used as an adjunctive therapeutic modality together with one or more other agents or therapeutic modalities. In some embodiments the cells are used both as primary and as adjunctive therapeutic agents and/or modalities. In both regards, the cells can be used alone in the primary and/or in the adjunctive modality. They also can fee used together with other therapeutic agents or modalities, in the primary or in the adjunctive modality or both.

As discussed above, a primary treatment, such as a therapeutic agent, therapy, and/or therapeutic modality, targets (that is, is intended to act on) the primary dysfunction, such as a disease, that, is to be treated. An adjunctive treatment, such as a therapy and/or a therapeutic modality, san be administered in combination with a primary treatment, such as a therapeutic agent, therapy, and/or therapeutic modality, to act on the primary dysfunction, such as a disease, and supplement the effect of the primary treatment, thereby increasing the overall efficacy of the treatment regimen. An adjunctive treatment, such as an agent, therapy, and/or therapeutic modality, also can be administered, to act on complications and/or side effects of a primary dysfunction, such as a disease, and/or those caused by a treatment, such as a therapeutic agent, therapy, and/or therapeutic modality. In regard to any of these uses, one, two, three, or more primary treatments may be used together with one, two, three, or more adjunctive treatments.

In some embodiments MAPCs are administered to a subject prior to onset of a dysfunction, such as a disease and/or side effect. In embodiments the cells are administered while the dysfunction is developing. In some, embodiments the cells are administered after the dysfunction has been established. MAPCs can be administered at any stage n the development, persistence, and/or propagation of the dysfunction or after it recedes.

As discussed above, embodiments of the invention provide cells and methods for primary or adjunctive therapy. In certain embodiments of the invention, the cells are administered to an allogeneic subject. In some embodiments they are autologous to the subject. In some embodiments they are syngeneic to the subject. In some embodiments the cells are xenogeneic to a subject. Whether allogeneic, autologous, syngeneic, or xenogeneic, in various embodiments of the invention the MAPCs are only weakly immunogenic or are non-immunogenic in the subject. In embodiments the MAPCs have sufficiently low immunogenicity or are non-immunogenic and are sufficiently free of deleterious immune responses in general, that when administered to allogeneic subjects they can be used as "universal" donor cells without tissue typing and matching. In accordance with, various embodiments of the invention the MAPCs can also be stored and maintained in cell banks, and thus can be kept available for use when needed.

Furthermore in this regard MAPCs in various embodiments can be administered without adjunctive immunosuppressive treatment.

In all of these regards and others, embodiments of the invention provide MAPCs from mammals, including in one embodiment humans, and in other embodiments non-human primates, rats and mice, and dogs, pigs, goats, sheep, horses, and cows. MAPCs prepared from mammals as described above can be used in all of the methods and other aspects of the invention described herein.

MAPCs in accordance with various embodiments of the invention can be isolated from a variety of compartments and tissues of such mammals in which they are found, including but not limited to, bone marrow, peripheral blood, cord blood, blood, spleen, liver, muscle, brain, adipose tissue, placenta and others discussed below. MAPCs in some embodiments are cultured before use.

In some embodiments MAPCs are genetically engineered, such as to improve their immunomodulatory properties. In some embodiments genetically engineered MAPCs are produced by in vitro culture. In some embodiments genetically engineered MAPCs are produced from a transgenic organism.

Mechanisms of Action of MAPCs

Without being limited to any one or more explanatory mechanisms for the properties, activities, and effects of MAPCs, it is worth noting that they can exert beneficial effects, such as of treatment with MAPCs, through a variety of modalities. For instance, MAPCs can have directly beneficial effects. Such direct effects can be primarily a matter of direct contact between MAPCs and cells of a host. The contact may be with structural members of the cells or with constituents in their immediate environment. Such direct mechanisms may involve direct contact, diffusion, uptake, or other processes well known to those skilled in the art. The direct activities and effects of the MAPCs may be limited spatially, such as to an area of local deposition or to a bodily compartment accessed by injection.

MAPCs also can "home" in response to "homing" signals, such as those released at sites of injury or disease. Since homing often is mediated by signals whose natural function is to recruit cells to the sites where repairs are needed, the homing behavior can be a powerful tool for concentrating MAPCs to therapeutic targets. This effect can be stimulated by specific factors, as discussed below.

MAPCs may also modulate beneficial effects, as of treatments with MAPCs, by their response to factors. This may occur additionally or alternatively to direct modulation. Such factors may include homing factors, mitogens, and other stimulatory factors. They may also include differentiation factors, and factors that trigger particular cellular processes. Among the latter are factors that cause the secretion by cells of other specific factors, such as those that are involved in recruiting cells, such as stem cells (including MAPCs), to a site of injury or disease.

MAPCs may, in addition to the foregoing or alternatively thereto, secrete factors that act on endogenous cells, such as stem cells or progenitor cells. The factors may act on other cells to engender, enhance, decrease, or suppress their activities. MAPCs may secrete factors that act on stem, progenitor, or differentiated cells causing those cells to divide and/or differentiate. MAPCs that home to a site where repair is needed may secrete trophic factors that attract other cells to the site. In this way, MAPCs may attract stem, progenitor, or differentiated cells to a site where they are needed. MAPCs also may secrete factors that cause such cells to divide or differentiate.

Secretion of such factors, including trophic factors, can contribute to the efficacy of MAPCs in, for instance, limiting inflammatory damage, limiting vascular permeability, improving cell survival, and engendering and/or augmenting homing of repair cells to sites of damage. Such factors also may affect T-cell proliferation directly. Such factors also may affect dendritic cells, by decreasing their phagocytic and antigen presenting activities, which also may affect T-cell activity By these and other mechanisms, MAPCs can provide beneficial effects in the treatment of a variety of injuries, dysfunctions, disorders, and diseases.

MAPC Administration

MAPC Preparations

MAPCs can be prepared from a variety of tissues, such as bone marrow cells, as discussed in greater detail elsewhere herein.

In many embodiments the purity of MAPCs for administration to a subject is about 100%. In other embodiments it is 95% to 100%. In some embodiments it is 85% to 95%. Particularly in the case of admixtures wife other cells, the percentage of MAPCs can be 2%-5%, 3%-7%, 5%-10%, 7%-15%, 10%-15%, 10%-20%, 15%-20%, 20%-25%, 25%-30%, 30%-35%, 35%-40%, 40%-45%, 45%-50%, 60%-70%, 70%-80%, 80%-90%, or 90%-95%.

The number of MAPCs in a given volume can be determined by well known and routine procedures and instrumentation, using the presence and/or absence of certain markers, including those described herein, such as telomerase, and, where desirable the ability to differentiate into cells of more than one of the three primitive lineages as described herein. The percentage of MAPCs in a given volume of a mixture of cells can be determined by counting cells (such as the cells in an aliquot of a sample) and determining the number of cells that are MAPCs using the aforementioned procedures for identifying MAPCs. Cells can be readily counted manually or by using an automatic cell counter. MAPCs can be determined, such as MAPCs in a given volume, by specific staining, such as with specific binding reagents, often antibodies conjugated to a fluorescent label, followed by visual examination and counting or by automated identification and counting instrumentation, such as by a FACS (fluorescence activated cell sorter) instrument.

Treatment of disorders or diseases or the like with MAPCs may be with undifferentiated MAPCs, Treatment also may be with MAPCs that have been treated so that they are committed to a differentiation pathway. Treatment also may involve MAPCs that have been treated to differentiate into a less potent stem cell with limited differentiation potential. It also may involve MAPCs that have been treated to differentiate into a terminally differentiated cell type. The best type or mixture of MAPCs will be determined by the particular circumstances of their use, and it will be a matter of routine design for those skilled in the art to determine an effective type or combination of MAPCs in this regard.

Formulations

The choice of formulation for administering MAPCs for a given application will depend on a variety of factors. Prominent among these will be the species of subject, the nature of the disorder, dysfunction, or disease being treated and its state and distribution in the subject, the nature of other therapies and agents that are being administered, the optimum route for administration of the MAPCs, survivability of MAPCs via the route, the dosing regimen, and other factors that will be apparent to those skilled in the art. In particular, for instance, the choice of suitable carriers and other additives will depend on the exact route of administration and the nature of the particular dosage form.

Cell survival may be an important determinant of the efficacy of therapies using MAPCs. This is true for both primary and adjunctive therapies. Another concern arises when target sites are inhospitable to cell seeding and cell growth. This may impede access to the site and/or engraftment there of therapeutic MAPCs. In embodiments the invention comprises the use of measures to increase cell survival and/or to overcome problems posed by barriers to seeding and/or growth.

Examples of compositions comprising MAPCs include liquid preparations, including solutions, suspensions, and preparations for intramuscular or intravenous administration (e.g., Injectable administration), such as sterile suspensions or emulsions. Such compositions may comprise an admixture of MAPCs with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, flavoring agents, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Compositions of the invention often are conveniently provided as liquid preparations, e.g., isotonic aqueous solutions, suspensions, emulsions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

Various additives often will be included to enhance the stability, sterility, and isotonicity of the compositions, such as antimicrobial preservatives, antioxidants, chelating agents, and buffers, among others. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form, can be brought about by the use of agents that delay absorption, for example, aluminum monostearate, and gelatin. According to the present invention, however, any vehicle, diluent, or additive used would have to be compatible with the cells.

MAPC solutions, suspensions, and gels often contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose) may also be present.

Often the compositions will be isotonic, i.e., they will have the same osmotic pressure as blood, and lacrimal fluid when properly prepared for administration.

The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

Viscosity of the compositions, if desired, can be maintained, at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically acceptable preservative or cell stabilizer can be employed to increase the life of MAPC compositions. If such preservatives are included, it is well within the purview of the skilled artisan to select compositions that will not affect the viability or efficacy of the MAPCs.

Those skilled in the art will recognize that the components of the compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells utilized in practicing the present invention in the required amount of the appropriate solvent with various amounts of the other ingredients, as desired.

Also preferred are solutions for injection, including stereotactic injection and infusion, such as IV infusion.

In some embodiments, MAPCs are formulated in a unit dosage injectable form, such as a solution, suspension, or emulsion. Pharmaceutical formulations suitable for injection of MAPCs typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

For any composition to be administered to an animal or human, and for any particular method of administration, it is preferred to determine therefore: toxicity, such as by determining the lethal dose (LD) and LD50 in a suitable animal model, e.g., rodent such as mouse or rat; and, the dosage of the composition(s), concentration of components therein, and timing of administering the composition(s), which elicit a suitable response. Such determinations do not require undue experimentation from the knowledge of fee skilled artisan, this disclosure, and the documents cited herein. And, the time for sequential administrations can be ascertained without undue experimentation.

In some embodiments MAPCs are encapsulated for administration, particularly where encapsulation enhances the effectiveness of the therapy, or provides advantages in handling and/or shelf life. Encapsulation in some embodiments where it increases the efficacy of MAPC mediated immunosuppression may, as a result, also reduce the need for immunosuppressive drug therapy.

Also, encapsulation in some embodiments provides a barrier to a subject's immune system that may further reduce a subject's immune response to the MAPCs (which generally are not immunogenic or are only weakly immunogenic in allogeneic transplants), thereby reducing any graft rejection or inflammation that might occur upon administration of the cells.

In a variety of embodiments where MAPCs are administered in admixture with cells of another type, which are more typically immunogenic in an allogeneic or xenogeneic setting, encapsulation may reduce or eliminate adverse host immune responses to the non-MAPC cells and/or GVHD that might occur in an immunocompromised host if the admixed cells are immunocompetent and recognize the host as non-self.

MAPCs may be encapsulated by membranes, as well as capsules, prior to implantation. It is contemplated that any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval.

A wide variety of materials may be used in various embodiments for microencapsulation of MAPCs. Such materials include, for example, polymer capsules, alginate-poly-L-lysine-alginate microcapsules, barium poly-L-lysine alginate capsules, barium alginate capsules, polyacrylonitrile/polyvinylchloride (FAN/PVC) hollow fibers, and polyethersulfone (PES) hollow fibers.

Techniques for microencapsulation of cells that may be used for administration of MAPCs are known to those of skill in the art and are described, for example, in Chang, P., et al., 1999; Matthew, H. W., et al, 1991; Yanagi, K., et al., 1989; Cai Z. H., et al., 1988; Chang, T. M., 1992 and in U.S. Pat. No. 5,639,275 (which, for example, describes a biocompatible capsule for long-term maintenance of cells that stably express biologically active molecules). Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of MAPCs.

Certain embodiments incorporate MAPCs into a polymer, such as a biopolymer or synthetic polymer. Examples of biopolymers include, but are not limited to, fibronectin, fibin, fibrinogen, thrombin, collagen, and proteoglycans. Other factors, such as the cytokines discussed above, can also be incorporated into the polymer. In other embodiments of the invention, MAPCs may be incorporated in the interstices of a three-dimensional gel. A large polymer or gel, typically, will be surgically implanted. A polymer or gel that can be formulated in small enough particles or fibers can be administered by other common, more convenient, non-surgical routes.

Pharmaceutical compositions of the invention may be prepared in many forms that include tablets, hard or soft gelatin capsules, aqueous solutions, suspensions, and liposomes and other slow-release formulations, such as shaped polymeric gels. Oral liquid pharmaceutical compositions may be in the form of, for example, aqueous or oily suspensions, solutions, emulsions, syrups, or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives. An oral dosage form may be formulated such that cells are released into the intestine after passing through the stomach. Such formulations are described in U.S. Pat. No. 6,306,434 and in the references contained therein.

Pharmaceutical compositions suitable for rectal administration can be prepared as unit dose suppositories. Suitable carriers include saline solution and other materials commonly used in the art.

For administration by inhalation, cells can be conveniently delivered from an insufflator, nebulizer, or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, a means may take the form of a dry powder composition, for example, a powder mix of a modulator and a suitable powder base such as lactose or starch. The powder composition may be presented in unit dosage form in, for example, capsules or cartridges or, e.g., gelatin or blister packs, from which the powder may be administered with the aid of an inhalator or insufflator. For Intra-nasal administration, cells may be administered via a liquid spray, such as via a plastic bottle atomizer.

Other Active Ingredients

MAPCs may be administered with other pharmaceutically active agents. In some embodiments one or more of such agents are formulated together with MAPCs for administration. In some embodiments the MAPCs and the one or more agents are in separate formulations. In sense embodiments the compositions comprising the MAPCs and/or the one or more agents are formulated with regard to adjunctive use with one another.

MAPCs may be administered in a formulation comprising immunosuppressive agents, such as any combination of any number of a corticosteroid, cyclosporin A, a cyclosporin-like immunosuppressive agent, cyclophosphamide, antithymocyte globulin, azathioprine, FK-506, and a macrolide-like immunosuppressive agent other than FK-506 and rapamycin. In certain embodiments, such agents include a corticosteroid, cyclosporin A, azathioprine, cyclophosphamide, rapamycin, and/or FK-506. Immunosuppressive agents in accordance with the foregoing may be the only such additional agents or may be combined with other agents, such as other agents noted herein. Other immunosuppressive agents include Tacrolimus, Mycophenolate mofetil, and Sirolimus.

Such agents also include antibiotic agents, antifungal agents, and antiviral agents, to name just a few other pharmacologically active substances and compositions that may be used in accordance with embodiments of the invention.

Typical antibiotics or anti-mycotic compounds include, but are not limited to, penicillin, streptomycin, amphotericin, ampicillin, gentamicin, kanamycin, mycophenolic acid, nalidixic acid, neomycin, nystatin, paromomycin, polymyxin, puromycin, rifampicin, spectinomycin, tetracycline, tylosin, zeocin, and cephalosporins, aminoglycosides, and echinocandins.

Further additives of this type relate to the fact that MAPCs, like other stem cells, following administration to a subject may "home" to an environment favorable to their growth and function. Such "homing" often concentrates the cells at sites where they are needed, such as sites of immune disorder, dysfunction, or disease. A number of substances are known to stimulate homing. They include growth factors and trophic signaling agents, such as cytokines. They may be used to promote homing of MAPCs to therapeutically targeted sites. They may be administered to a subject prior to treatment with MAPCs, together with MAPCs, or after MAPCs are administered.

Certain cytokines, for instance, alter or affect the migration of MAPCs or their differentiated counterparts to sites in need of therapy, such as immunocompromised sites. Cytokines that may be used in this regard include, but are not limited to, stromal cell derived factor-1 (SDF-1), stem cell factor (SCF), angiopoietin-1, placenta-derived growth factor (PlGF), granulocyte-colony stimulating factor (G-CSF), cytokines that stimulate expression of endothelial adhesion molecules such as ICAMs and VCAMs, and cytokines that engender or facilitate homing.

They may be administered to a subject as a pre-treatment, along with MAPCs, or after MAPCs have been administered, to promote homing to desired sites and to achieve improved therapeutic effect, either by improved homing or by other mechanisms. Such factors may be combined with MAPCs in a formulation suitable for them to be administered together. Alternatively, such factors may be formulated and administered separately.

Order of administration, formulations, doses, frequency of dosing, and routes of administration of factors (such as the cytokines discussed above) and MAPCs generally will vary with the disorder or disease being treated, its severity, the subject, other therapies that are being administered, the stage of the disorder or disease, and prognostic factors, among others. General regimens that have been established for other treatments provide a framework for determining appropriate dosing in MAPC-mediated direct or adjunctive therapy. These, together with the additional information provided herein, will enable the skilled artisan to determine appropriate administration procedures in accordance with embodiments of the invention, without undue experimentation.

In embodiments cells are formulated suitably for treating brain injury, including the brain injuries and/or dysfunctions and/or disorders and/or diseases set forth herein. In embodiments, the formulations are effective for parenteral administration. In embodiments the formulations are effective for I.V. infusion. In embodiments the formulations are effective for stereotactic injection.

Routes

MAPCs can be administered to a subject by any of a variety of routes known to those skilled in the art that may be used to administer cells to a subject.

In various embodiments the MAPCs are administered to a subject by any route for effective delivery of cell therapeutics. In some embodiments the cells are administered by injection, including local and/or systemic injection. In certain embodiments the cells are administered within and/or in proximity to the site of the dysfunction they are intended to treat. In some embodiments, the cells are administered by injection at a location not in proximity to the site of the dysfunction. In some embodiments the cells are administered by systemic injection, such as intravenous injection.

Among methods that may be used in this regard in embodiments of the invention are methods for administering MAPCs by a parenteral route. Parenteral routes of administration useful in various embodiments of the invention include, among others, administration by intravenous, intraarterial, intracardiac, intraspinal, intrathecal, intraosseous, intraarticular, intrasynovial, intracutaneous, intradermal, subcutaneous, and/or intramuscular injection. In some embodiments intravenous, intraarterial, intracutaneous, intradermal, subcutaneous and/or intramuscular injection are used. In some embodiments intravenous, intraarterial, intracutaneous, subcutaneous, and/or intramuscular injection are used.

In various embodiments of the invention MAPCs are administered by systemic injection. Systemic injection, such as intravenous injection, offers one of the simplest and least invasive routes for administering MAPCs. In some cases, these routes may require high MAPC doses for optimal effectiveness and/or homing by the MAPCs to the target sites. In a variety of embodiments MAPCs may be administered by targeted and/or localized injections to ensure optimum effect at the target sites.

MAPCs may be administered to the subject through a hypodermic needle by a syringe in some embodiments of the invention. In various embodiments, MAPCs are administered to the subject through a catheter. In a variety of embodiments, MAPCs are administered by surgical implantation. Further in this regard, in various embodiments of the invention, MAPCs are administered to the subject by implantation using an arthroscopic procedure. In some embodiments MAPCs are administered to the subject by stereotactic injection. In some embodiments MAPCs are administered to the subject in or on a solid support, such as a polymer or gel. In various embodiments, MAPCs are administered to the subject in an encapsulated form.

In additional embodiments of the invention, MAPCs are suitably formulated for oral, rectal, epicutaneous, ocular, nasal, and/or pulmonary delivery and are administered accordingly.

In embodiments parenteral administration is used for treating brain injury, including the brain injuries and/or dysfunctions and/or disorders and/or diseases set forth herein. In embodiments, IV infusion is used. In embodiments stereotactic injection is used.

Dosing

Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of MAPCs appropriate to be used in accordance with various embodiments of the invention will depend on numerous factors. It may vary considerably for different circumstances. The parameters that will determine optimal doses of MAPCs to be administered for primary and adjunctive therapy generally will include some or all of the following: the disease being treated and its stage: the species of the subject, their health, gender, age, weight, and metabolic rate; the subject's immunocompetence; other therapies being administered; and expected potential complications from the subject's history or genotype. The parameters may also include: whether the MAPCs are syngeneic, autologous, allogeneic, or xenogeneic; their potency (specific activity); the site and/or distribution that must be targeted for the MAPCs to be effective; and such characteristics of the site such as accessibility to MAPCs and/or engraftment of MAPCs. Additional parameters include co-administration with MAPCs of other factors (such as growth factors and cytokines). The Optimal dose in a given situation also will take into consideration the way in which the cells are formulated, the way they are administered, and the degree to which the cells will be localized at the target sites following administration. Finally, the determination of optimal dosing necessarily will provide an effective dose that is neither below the threshold of maximal beneficial effect nor above the threshold where the deleterious effects associated with the dose of MAPCs outweighs the advantages of the increased dose.

The optimal dose of MAPCs for some embodiments will be in the range of doses used for autologous, mononuclear bone marrow transplantation. It can be estimated by extrapolation from animal studies taking into account differences in size (mass) and metabolic factors, and from dosage requirements established for other cell therapies, such as transplant therapies.

In embodiments optimal doses range from $10^4$ to $10^9$ MAPC cells/kg of recipient mass per administration. In embodiments optimal doses per administration will be between $10^5$ to $10^8$ MAPC cells/kg. In embodiments optimal dose per administration will be $5 \times 10^8$ to $5 \times 10^7$ MAPC cells/kg. In embodiments optimal doses per administration will be any of 1, 2, 3, 4, 5, 6, 7, 8, or $9 \times 10^6$ to any of 1, 2, 3, 4, 5, 6, 7, 8, or $9 \times 10^7$.

By way of reference, some of the mid-high doses in the foregoing are analogous to the doses of nucleated cells used in autologous mononuclear bone marrow transplantation. Some of the mid-lower doses are analogous to the number of $CD34^+$ cells/kg used in autologous mononuclear hone marrow transplantation.

It is to be appreciated that a single dose may be delivered all at once, fractionally, or continuously over a period of time. The entire dose also may be delivered to a single location or spread fractionally over several locations.

In various embodiments, MAPCs may be administered in an initial dose, and thereafter maintained by further administration of MAPCs. MAPCs may be administered by one method initially, and thereafter administered by the same method or one or more different methods. The subject's MAPC levels can be maintained by the ongoing administration of the cells. Various embodiments administer the MAPCs either initially or to maintain their level in the subject or both by intravenous injection. In a variety of embodiments, other forms of administration, are used, dependent upon the patient's condition, and other factors, discussed elsewhere herein.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regiment can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer MAPCs.

In some embodiments MAPCs are administered to a subject in one dose. In others MAPCs are administered to a subject in a series of two or more doses in succession. In some other embodiments wherein MAPCs are administered in a single dose, in two doses, and/or more than two doses, the doses may be the same or different, and they are administered with equal or with unequal intervals between them.

MAPCs may be administered in many frequencies over a wide range of times, such as until a desired therapeutic effect is achieved. In some embodiments, MAPCs are administered over a period of less than one day. In other embodiment they are administered over two, three, four, five, or six days. In some embodiments MAPCs are administered one or more times per week, over a period of weeks. In other embodiments they are administered over a period of weeks for one to several months. In various embodiments they may be administered over a period of months. In others they may be administered over a period of one or more years. Generally lengths of treatment will be proportional to the length of the disease process, the effectiveness of the therapies being applied, and the condition and response of the subject being treated.

In some embodiments, MAPCs are administered one time, two times, three times, or more than three times until a desired therapeutic effect is achieved or administration no longer appears to be likely to provide a benefit to the subject. In some embodiments MAPCs are administered continuously for a period of time, such as by intravenous drip. Administration of MAPCs may be for a short period of time, for days, for weeks, for months, for years, or for longer periods of time.

In embodiments, a single bolus is administered to treat brain injuries, including the brain injuries and/or dysfunctions and/or disorders and/or diseases set forth herein. In embodiments two or more administrations of a single bolus are administered separated in time by one or more days. In embodiments each dose is administered by I.V. infusions over any period of time from several minutes to several hours. In embodiments a single dose of cells is administered by stereotactic injection. In embodiments, two or more doses are administered to the same or different areas of the brain by stereotactic injection. In embodiments involving bolus, IV, and stereotactic injection, for treating brain injury in this regard, the dose of cells per administration is from $10^4$ to $10^9$ MAPC cells/kg of recipient mass per administration. In embodiments the dose is from $10^5$ to $10^8$ MAPC cells/kg. In embodiments the dose is from $5 \times 10^5$ to $5 \times 10^7$ MAPC cells/kg. In embodiments the dose is 1, 2, 3, 4, 5, 6, 7, 8, or $9 \times 10^6$ to any of 1, 2, 3, 4, 5, 6, 7, 8, or $9 \times 10^7$.

MAPCs as Described in U.S. Pat. No. 7,015,037

Human MAPCs are described in the art. Methods off MAPC isolation for humans and mouse are known in the art. It Is therefore now possible for one of skill in the art to obtain bone marrow aspirates, brain or liver biopsies, and other organs, and isolate the cells using positive and/or negative selection techniques available to those of skill in the art, relying upon the genes that are expressed (or not expressed) in these cells (e.g., by functional or morphological assays such as those disclosed in the above-referenced applications, which have been incorporated herein by reference). Illustrative methods are described in, for instance, U.S. Pat. No. 7,015,037, the contents of which are incorporated herein by reference for a description of MAPCs and methods of preparation.

Isolation and Growth of MAPCs as Described in U.S. Pat. No. 7,015,037

Methods of MAPC isolation are known in fee art from, for instance, humans, rat, mouse, dog and pig. Illustrative methods are described in, for instance, U.S. Pat. No. 7,015, 037 and PCT/US02/04652 (published as WO 02/064748), and these methods, along with a characterization of MAPCs disclosed therein, by way of illustration and non-limiting example only, are incorporated herein by reference.

MAPCs were initially isolated from bone marrow, and were subsequently established from other tissues, including brain and muscle (Jiang, Y. et al., 2002). MAPCs can be isolated from many sources, including, but not limited to bone marrow, placenta, umbilical cord and cord blood, muscle, brain, liver, spinal cord, blood, adipose tissue and skin. For example, MAPCs can be derived from bone marrow aspirates, which can be obtained by standard means available to those of skill in the art (see, for example, Muschler, G. F., et al., 1997; Batinic, D., et al., 1990).

Human MAPC Phenotype Under Conditions Set Forth in U.S. Pat. No. 7,015,037

Immunophenotypic analysis by FACS of human MAPCs obtained after 22-25 cell doublings indicated that the cells do act express CD31, CD34, CD36, CD38, CD45, CD50, CD62E and -P, HLA-DR, Muc18, STRO-1, cKit, Tie/Tek; and express low levels of CD44, HLA-class 1, and βB-microglobulin, but express CD10, CD13, CD49b, CD49e, CDw90, Flk1 (N>10).

Once cells underwent >40 doublings in cultures re-seeded at about $2 \times 10^3/cm^2$, the phenotype became more homogenous, and no cell expressed HLA class-I or CD44 (n=6). When cells were grown at higher confluence, they expressed high levels of Muc18, CD44, HLA class I, and β2-microglobulin, which is similar to the phenotype described for MSC (N=8) (Pittenger, 1999).

Immunohistochemistry showed that human MAPCs grown at about $2 \times 10^3/cm^2$ seeding density expressed EGF-R, TGF-R1 and -2, BMP-R1A, PDGF-R1a and -B, and that a small subpopulation (between 1 and 10%) of MAPCs stained wife anti-SSEA4 antibodies (Kannagi, R, 1983).

Using Clontech cDNA arrays the expressed gene profile of human MAPCs cultured at seeding densities of about $2 \times 10^3$ cells/cm² for 22 and 26 cell doublings was determined:

A. MAPCs did not express CD31, CD36, CD62E, CD62P, CD44-H, cKit, Tie, receptors for IL1, IL3, IL6, IL11, G CSF, GM-CSF, Epo, Flt3-L, or CNTF, and low levels of HLA-class-I, CD44-E and Muc-18 mRNA.

B. MAPCs expressed mRNA for the cytokines BMP1, BMP5, VEGF, HGF, KGF, MCP1; the cytokine receptors Flk1, EGF-R, PDGF-R1α, gp130, LIF-R, activin-R1 and -R2, TGFR-2, BMP-R1A; the adhesion receptors CD49c, CD49d, CD29; and CD10.

C. MAPCs expressed mRNA for hTRT and TRF1; the POU domain transcription factor oct-4, sox-2 (required with oct-4 to maintain undifferentiated state of ES/EC, Uwanogho D., 1995), sox 11 (neural development), sox 9 (chondrogenesis) (Lefebvre V., 1998); homeodeomain transcription factors: Hox-a4 and -a5 (cervical and thoracic skeleton specification; organogenesis of respiratory tract) (Packer AI, 2000), Hox-a9 (myelopoiesis) (Lawrence H, 1997), Dlx4 (specification of forebrain and peripheral structures of head) (Akimenko Mass., 1994), MSX1 (embryonic mesoderm, adult heart and muscle, chondro- and osteogenesis) (Foerst-Potts L. 1997), PDX1 (pancreas) (Offield M F, 1996).

D. Presence of oct-4, LIF-R, and hTRT mRNA was confirmed by RT-PCR.

E. In addition, RT-PCR showed that rex-1 mRNA and rox-1 mRNA were expressed in MAPCs.

Oct-4, rex-1 and rox-1 were expressed in MAPCs derived from human and murine marrow and from murine liver and brain. Human MAPCs expressed LIF-R and stained positive with SSEA-4. Finally, oct-4, LIF-R, rex-1 and rox-1 mRNA levels were found to increase in human MAPCs cultured beyond 30 cell doublings, which resulted in phenotypically more homogenous cells. In contrast, MAPCs cultured at high density lost expression of these markers. This was associated with senescence before 40 cell doublings and loss of differentiation to cells other than chondroblasts, osteoblasts, and adipocytes. Thus, the presence of oct-4, combined with rex-1, rox-1, and sox-2, correlated with the presence of the most primitive cells in MAPCs cultures.

Methods for culturing MAPCs are well-known in the art. (See for instance, U.S. Pat. No. 7,015,037, which is herein incorporated by reference as to methods for culturing MAPCs.) The density for culturing MAPCs can vary from about 100 cells/cm² or about 150 cells/cm² to about 10,000 cells/cm², including about 200 cells/cm² to about 1500 cells/cm² to about 2000 cells/cm². The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 3 to 5%, can be used at any time during the isolation, growth, and differentiation of MAPCs in culture.

The present invention is additionally described by way of the following illustrative, non-limiting examples.

EXAMPLES

Figure 1:
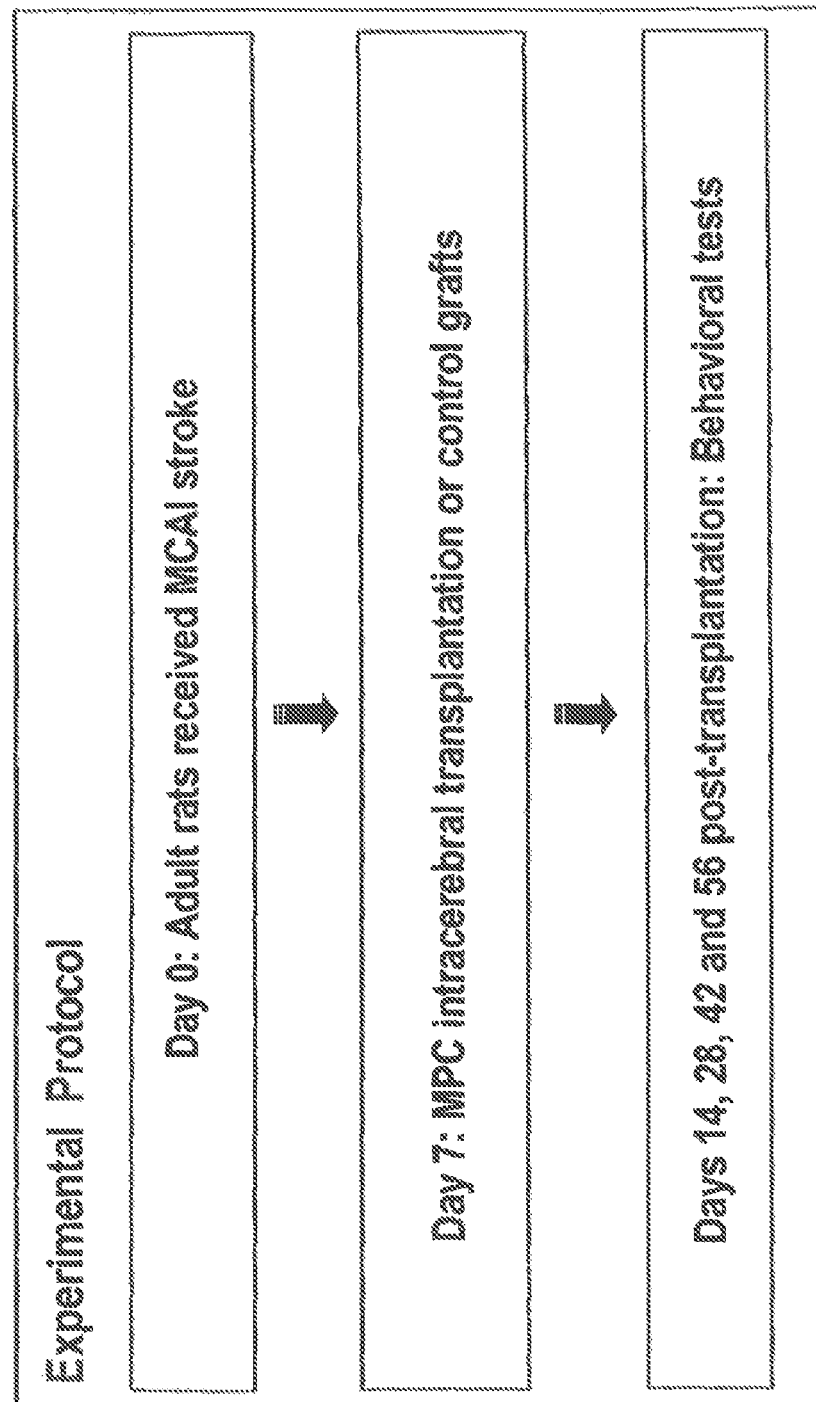
FIG. 1 is a flow chart showing the general experimental protocol used in certain of the examples herein described, as set forth in Example 1.

Example 1: Hypoxic-Ischemic Injury with MAPCs in Rats and Treatment with MAPCS and Immunosuppression Seven day old Sprague Dawley (SD) rat pups (n=7 per test group) were subjected to HI injury by the method of unilateral carotid ligation followed by 8% hypoxia, as described in Rice et al, *Ann Neurol.* 9: 131-141 (1981), which is herein incorporated by reference in its entirety particularly in regard to this method. Seven days after the injury, the animals underwent stereotaxic transplantation into the hippocampal region with cryopreserved MAPCs (thawed just prior to transplantation) derived from either SD rats (syngeneic, GFP-labeled, 200,000 cells per animal) or Fisher rats (allogeneic, β-gal-labeled, 200,000 cells per animal). All animals were treated with daily immunosuppression (CSA, 1 mg/kg, i.p.) throughout the survival period. On days 7 and 14 post-transplantation, the Elevated Body Swing Test (EBST) and Rotarod test were performed to reveal general and coordinated motor and neurological functions as described in Borlongan et al., *J Neurosci,* 15: 5372-5378 (1995) which is herein incorporated by reference in its entirety particularly in regard to these methods of assessing behavioral performance. Animals were euthanized for immunohistochemical analysis of grafted MAPCs after testing on day 14. A flow chart of the experiment is depicted in FIG. 1. No mortality was observed in animals receiving MAPC transplants during the course of the study.

Figure 2:
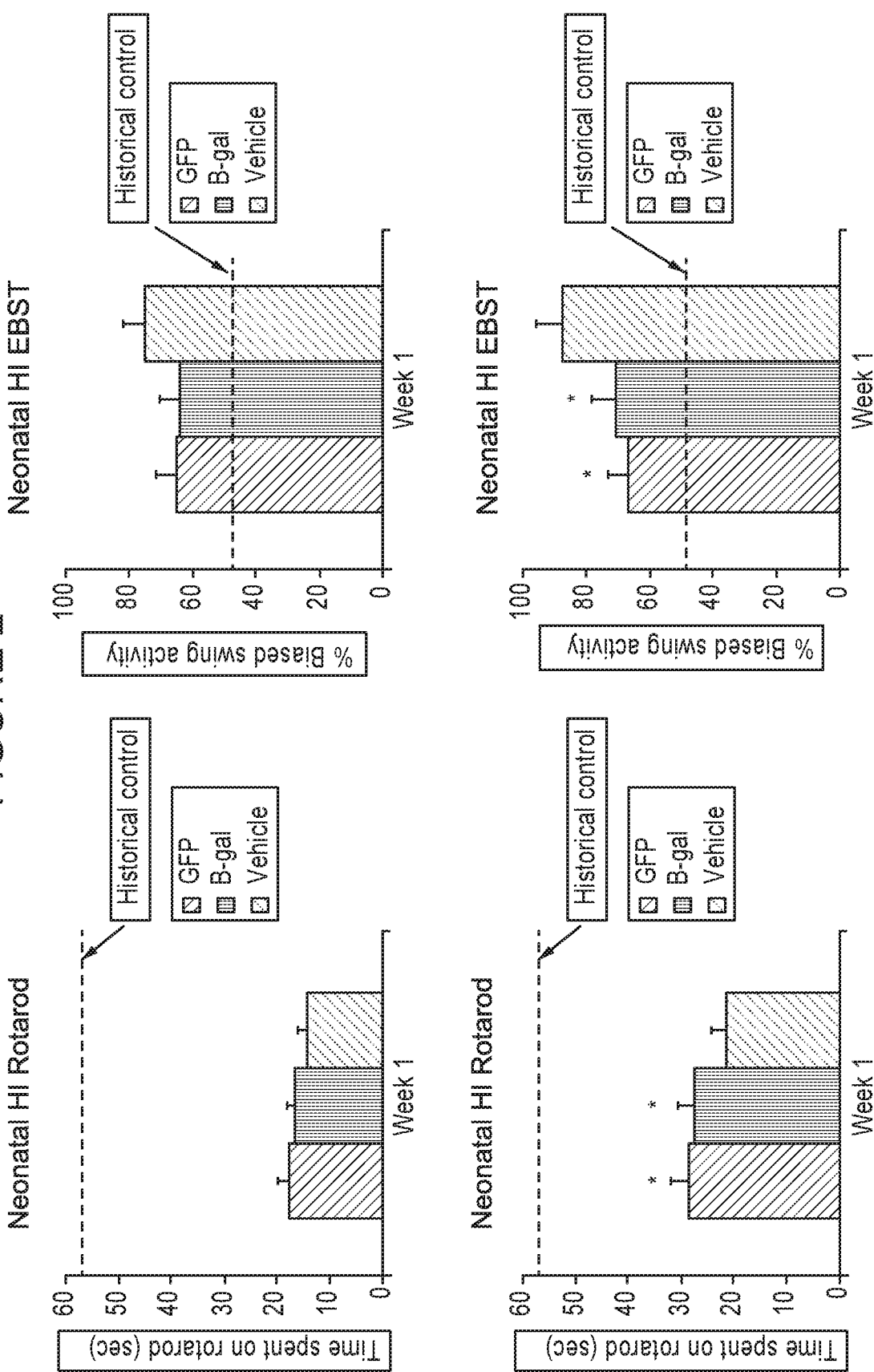
FIG. 2 is a set of graphs showing that syngeneic and allogeneic MAPC transplants promote behavioral recovery in neonatal HI rats, as described in Example 2. Behavioral tests for motor and neurological functions were conducted on days 7 and 14 on animals receiving syngeneic and allogeneic MAPC transplants. The animals initially exhibited a trend toward less behavioral deficits on day 7 after transplantation, and then showed significantly reduced motor abnormalities by day 14 post-transplantation compared to controls. Asterisks indicate statistical significance at $p<0.05$ versus negative controls (vehicle infusion).

Example 2A: Evaluation of Locomotor Skills at 7 and 14 Days after MAPC Injection in HI-Injury Rats Animals were treated as described in Example 1. At day 7 post-transplantation, MAPC transplanted HI Injured animals displayed a trend of less motor asymmetry as determined by the EBST (64%-65% versus 75%) and longer time spent on the rotarod (14.1-16.5 versus 18 seconds) compared to vehicle-infused injured animals. At day 14 post-transplantation, MAPC transplanted animals exhibited significantly reduced motor asymmetry (66%-70% versus 87%) and longer time spent on the rotarod (27.3-28.3 versus 21 seconds) than those control animals that: received the vehicle infusion. Syngeneic and allogeneic MAPCs transplanted into injured animals did not differ statistically in their behavioral improvements at both test periods. Results are depicted graphically in FIG. 2. The results show the therapeutic effects of injected MAPCs in the rat HI injury model by both locomotor and neurological measures.

Example 2B: Histological Analysis of MAPC Engraftment on Day 14 after MAPC Injection in Brains of HI Rats Animals were treated as described in Example 1. Grafted MAPCs were detected in the brains of the HI-injured animals after sacrifice on Day 14 post transplantation by histological examination. GFP-positive syngeneic grafts were detected mostly in the original hippocampal CA3 transplant site and adjacent CA2 region, which co-labeled with DAPI. Allogeneic grafts, detected by anti-β-gal staining and co-labeling with DAPI, displayed a similar pattern of graft survival in HI injured brains. Graft survival was 0.96% at 14 days (ANOVA F value is 24.27, df=2, 19 and p<0.0001; Fisher posthoc is p<0.0001), The results show that both allogeneic and syngeneic MAPCs engraft at the injection site and persist to at least two weeks after direct intracerebral injection in animals in the rat HI injury model.

Example 3: Engrafted MAPCs Protect Endogenous Neurons

Figure 3:
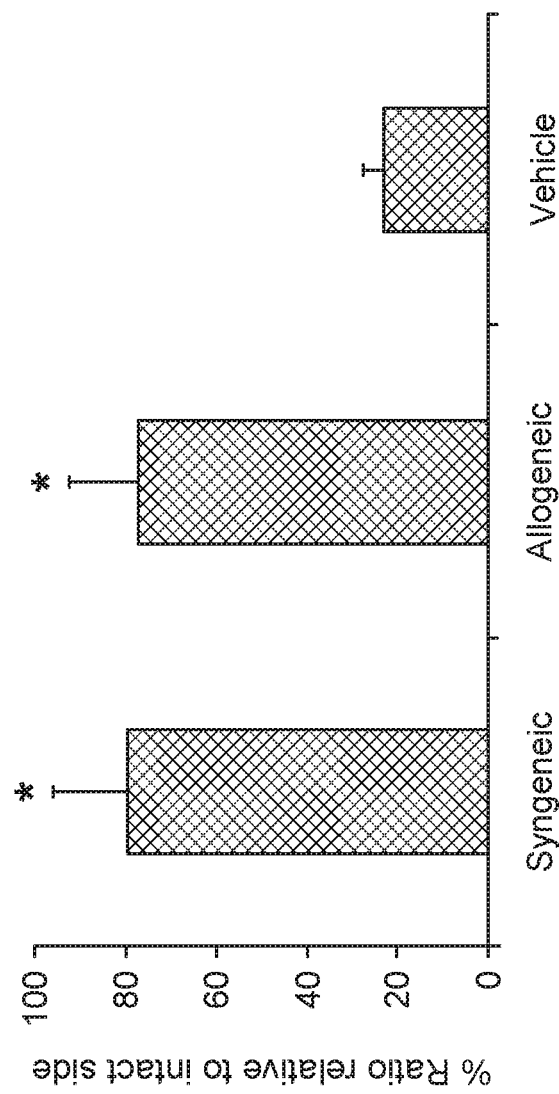
FIG. 3 is a graph showing that MAPC grafts reduce CA3 neuronal cell loss in HI injured animals, as described in Example 3. The graph shows viable cells observed by histological analysis of hippocampus sections. Animals were sacrificed on day 14 after transplantation of MAPCs. Brain sections were prepared, Nissl stained, and examined for neuronal viability in hippocampi of MAPC and vehicle treated animals. Viable cells per field were counted in both the injured and the uninjured contralateral hippocampal fields of each section, and these counts were compared. Uninjured hippocampus cell counts were taken as 100%. The data demonstrate statistically significant protection of neurons in the CA3 region following MAPC transplantation (ANOVA F value is 35.33, df=2, 19 and $p<0.0001$; Fisher posthoc is $p<0.0001$).

Animals were treated as described in Example 1, Histological analysis was carried out much as described in Example 2B, but alternate brain sections were Nissl stained to determine the level of endogenous neuronal viability. There was a significant decrease in endogenous neuronal death in animals that were injected with syngeneic or allogeneic MAPCs, compared to animals injected with control vehicle. The results are depicted graphically in FIG. 3. The results show that MAPC administration protects endogenous neurons from hypoxic ischemic injury, resulting in increased neuronal viability.

Example 4: Co-Localization of Engrafted MAPCs and Neurons Shown by Marker Analysis Animals were treated as described in Example 1. Brain sections generated from the MAPC treated rats were co-stained for the MAPC markers described above (GFP for syngeneic MAPCs or β-gal for allogeneic MAPCs) and simultaneously for MAP2, a well characterized marker for neurons. A few cells expressing both the respective MAPC marker and the neuronal marker were found in both syngeneic and allogeneic engrailed animals, showing that some MAPCs have differentiated into neurons; although it is also possible that some double staining cells are the rare result of the fusion of an engrafted MAPC cell with an endogenous neuronal cell. The results show early phenotypic neuronal differentiation of MAPCs at day 14 after administration to animals in the rat HI injury model.

Example 5: MAPCs are Therapeutically Beneficial in the Neonatal Rat HI Injury Model without Immunosuppression when Administered by Stereotactic Injection or by I.V. Infusion Seven day old Sprague Dawley (SD) rat pups (n=7 per test group) were subjected to HI injury by unilateral carotid ligation followed by 8% hypoxia, as described in Example 1 above and in the reference cited therein. Seven days after HI injury the animals underwent stereotaxic transplantation into the hippocampal region with, cryopreserved MAPCs (thawed, just prior to transplantation) derived from Fisher rats (allogeneic, β-gal-labeled, 200,000 cells per animal). Behavioral tests were conducted on post-transplantation days 7 and 14 using the EBST and the Rotarod test to reveal general and coordinated motor and neurological functions. By Day 14, MAPC treated animals showed statistically significant improvement in both the intracranial and IV delivered groups in both EBST and Rotarod tests, compared to the control group, which received PBS only (p<0.05 for both tests).

Example 6: Treatment of Strobe with Xenogeneic (Human) MAPCs in the MCA Occlusion Rodent Stroke Model Twenty-eight SD adult rats underwent middle cerebral artery (MCA) occlusion surgery to induce a surgical stroke in the animals. Seven days after the induction of stroke, animals were separated into four cohorts of seven animals each. Each cohort received direct intracerebral administration of one of the following: (1) 3 µl injection of PBS (control), (2) 3 µl injection of PBS containing 100,000 human MAPCs, (3) 3 µl injection of PBS containing 200,000 human MAPCs, and (4) 3 µl injection of PBS containing 400,000 human MAPCs. Animals were tested as described in the examples below, and sacrificed at day 21.

Figure 4:
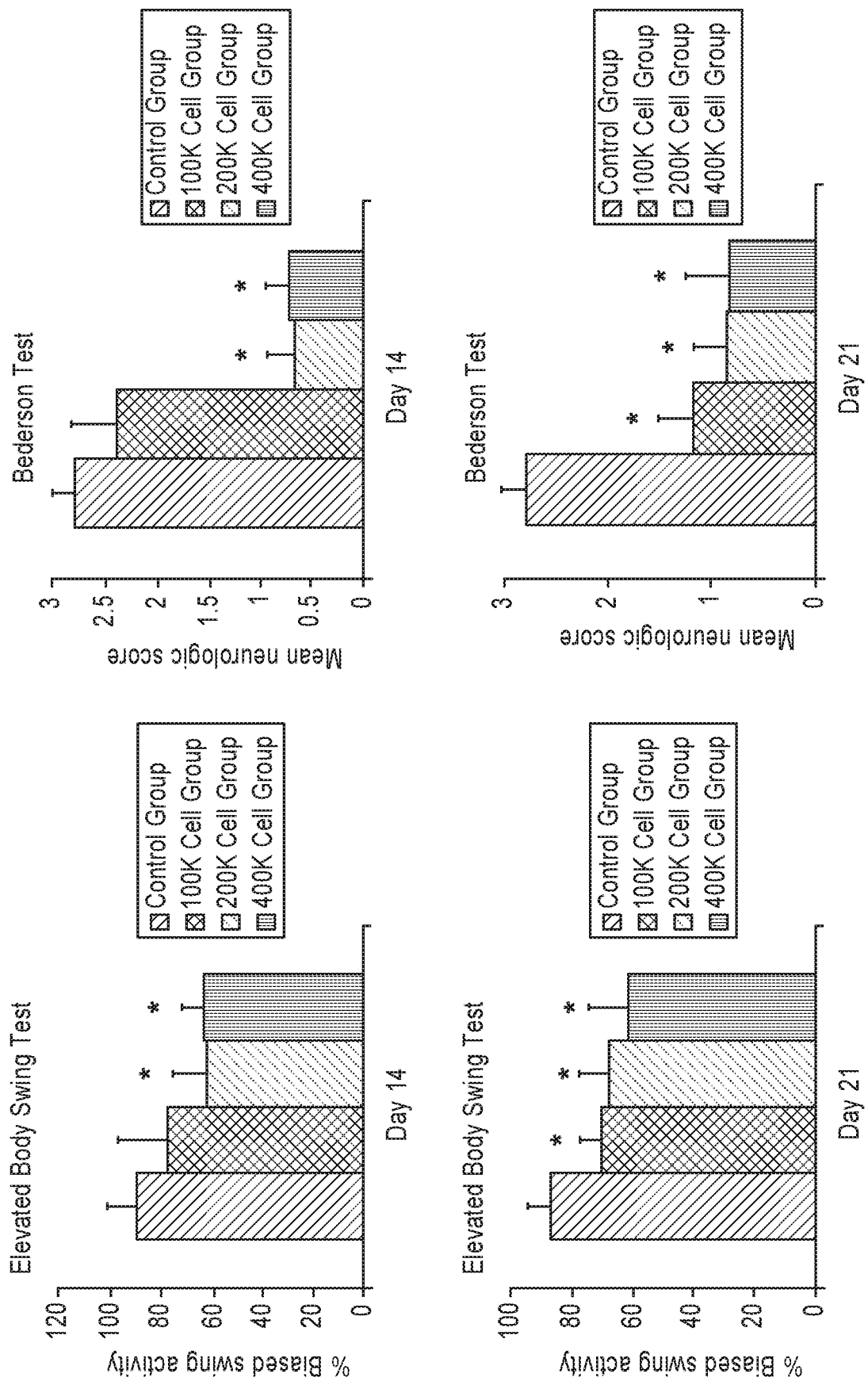
FIG. 4 is a set of graphs showing that xenogeneic MAPC transplants promote behavioral recovery in adult rats following surgically induced ischemic stroke, as described in Example 7. Behavioral tests for motor and neurological functions were conducted on days 14 and 21 after the induction of stroke (days 7 and 14 post-intracranial transplantation). Animals received 100,000, 200,000 and 400,000 xenogeneic MAPC cells or PBS as a vehicle only control.

Example 7: Therapeutic Benefit of MAPC Administration in the Stroke Model Demonstrated by Locomotor and Neurological Testing Animals were treated as described in Example 6. At 7 and 14 days after cell transplantation, each animal underwent an EBST and Bederson Test to determine locomotor and neurological function, as described above. A statistically significant improvement in swing bias in the EBST was observed in animals that received 200,000 or 400,000 cells compared to control at day 7 post transplantation. By 14 days, all three cohorts of animals receiving human MAPC injections showed significant improvement compared to the control group. Results are depicted in the upper and lower graphs on the left side of FIG. 4.

Concurrent but separate from the EBST, each rat was subjected to the Bederson panel of four tasks to evaluate neurological function at 14 and 21 days after MCA occlusion stroke. The four tests are scored from 0 (no observable neurological deficit) to 3 (severe neurological deficit) for each of the four tests. The four scores are then averaged to provide an overall measure of neurological function. At 7 days post MAPC transplantation, animals that received 200,000 or 400,000 cells showed a statistically significant improvement in neurological function, compared to control animals. By 14 days, all 3 cohorts receiving human MAPC injections demonstrated significant improvement compared to the control group. Results are depicted in the upper and lower graphs on the right side of FIG. 4.

The results show a dose dependent, statistically significant improvement of animals from the first test point (7 days post injection) in both locomotor and neurological testing as animals treated with 200,000 or 400,000 MAPCs. (Animals treated with 100,000 MAPCs did not display statistically significant improvement over animals treated only with the control vehicle.) The results demonstrate that administration of xenogeneic MAPCs by direct intracerebral injection to the rat stroke brain provide statistically significant improvement in both locomotor and neurological benefit tests when compared to vehicle only treated animals at least as early as one week after injection and persisting for at least as long as two weeks after injection.

Example 8: MAPC Engraftment in Brains in the Rat HI Stroke Model

Rats wire treated as described in Example 6 above. Following the last behavioral testing at day 14 after MAPC transplantation, the animals were sacrificed and the brains were harvested. Semi-thin sections of paraffin embedded tissue were stained with DAPI to visualize all cell nuclei and mouse anti-HuNu (human nuclei) polyclonal antibodies, followed by FITC-conjugated goat anti-mouse monoclonal antibodies to stain engrafted human MAPCs. MAPCs were found in the cortex (CTX), the sub-ventricular zone (SVZ), and the striatum (STR). The results show human MAPCs survive and engraft following intracerebral injection into rats that displayed significant therapeutic benefits of MAPC administration. The distribution of the cells shows that the MAPCs migrate to secondary regions of the brain and engraft there as well as at the primary site, where the cells were injected. Use same pattern of survival and migration was seen for injections of 100,000 and 200,000 MAPCs. There was no detectable HuNu immunoreactivity in the brains of control stroke animals that were injected with the vehicle only. Graft survival percentages were 0.55%, 0.7%, and 0.51% at 14 days after stroke for 100,000, 200,000, and 400,000 MAPC transplantation doses, respectively. The results show clearly that MAPCs survive and engraft in stroke model brains not only at the site of injection, but that they also migrate to and engraft at secondary sites away from the site of injection. In sum, to at least two weeks after direct intracerebral injection, xenogeneic human MAPCs are present at the site of injury and injection (the striatum), and at secondary sites in the injected brains, including the cortex and in the sub-ventricular zone.

Example 9: Treatment of Ischemic Stroke in a Rat Surgical Model with Allogeneic (Rat) MAPCs, with Xenogeneic (Human) MAPCs, Both with and without Concurrent Immunosuppression Treatment Thirty-five SD rats were subjected to middle cerebral artery (MCA) ligation surgery to induce a surgical stroke in the animals. Seven days after the Induction of stroke, the animals were separated into five cohorts of seven animals each. Each cohort received direct intracerebral administration of one of the following: (1) 3 µl injection of PBS containing 400,000 rat MAPCs with no immunosuppression; (2) 3 µl injection of PBS containing 400,000 rat MAPCs with immunosuppressive treatment (CSA, 1 mg/kg, i.p.); (3) 3 µl injection of PBS containing 400,000 human MAPCs with no immunosuppression; (4) 3 µl injection of PBS containing 400,000 human MAPCs with Immunosuppressive treatment (CSA, 1 mg/kg, i.p.), and (5) 3 µl injection of PBS containing 400,000 irradiated, non-viable human MAPCs with immunosuppressive treatment (CSA, 1 mg/kg, i.p.).

Example 10: Behavior and Neurological Assessment of Treatment of Ischemic Stroke in a Rat Surgical Modal with Allogeneic (Rat) MAPCs, with Xenogeneic (Human) MAPCs, Both with and without Concurrent Immunosuppression Treatment Animals were treated as described in Example 9. At 14 days after cell transplantation, and every 14 days thereafter for 8 weeks, each animal underwent an EBST and Bederson Test to determine locomotor and neurological function. Administration of xenogeneic and allogeneic MAPCs both resulted in statistically significant and sustained improvements in both EBST and Bederson assessments, with and without immunosuppressive treatment. The results show that MAPCs transplanted 7 days after ischemic injury provide statistically significant long term (8-week) sustained therapeutic benefits on behavior and neurological functions. The results further show that immunosuppression is not required for the demonstrated therapeutic effects. The results are depicted graphically in FIGS. 5 and 6.

Example 11: Treatment of Ischemic Stroke in a Rat Surgical Model with Xenogeneic (Human) MAPCs Delivered by Injection or by I.V. Infusion, with and without Immunosuppression Forty-two SD rats underwent middle cerebral artery (MCA) ligation surgery to Induce a surgical stroke in the animals. Seven days after the induction of stroke, animals were separated into six cohorts of seven animals each. Each cohort received intravenous administration of one of the following: (1) 400,000 human MAPCs with immunosuppressive treatment (CSA, 1 mg/kg, i.p.); (2) 400,000 human MAPCs with no immunosuppression; (3) 1,000,000 human MAPCs with immunosuppressive treatment (CSA, 1 mg/kg, i.p.); (4) 1,000,000 human MAPCs with no immunosuppressive treatment; (5) 1,000,000 Irradiated, non-viable human MAPCs with immunosuppressive treatment (CSA, 1 mg/kg, i.p.), and (6) 1,000,000 irradiated, non-viable human MAPCs with no immunosuppressive treatment.

Example 12: Treatment of Ischemic Stroke in a Rat Surgical Model with Xenogeneic (Human) MAPCs Delivered by Injection or by I.V. Infusion, with and without Immunosuppression—Behavioral and Neurological Evaluations Animals were treated as described in Example 11. At 14 days after cell transplantation, and every 14 days thereafter for 8 weeks, locomotor and neurological function of each animal was assessed by the EBST and Bederson tests, respectively.

Animals were sacrificed after testing on day 56 post transplantation.

The results show a significant dose dependent therapeutic effect on locomotor function. The animals infused with 1,000,000 viable MAPCs showed significant improvement over the corresponding control group treated with irradiated MAPCs. The same result was obtained with and without immunosuppression. There was no significant improvement in the animals infused with 400,000 viable MAPCs over the corresponding control group treated with irradiated MAPCs. The same result was obtained with and without immunosuppression.

The results also show a significant dose dependent effect on neurological function. Animals treated with both 400,000 and 1,000,000 viable MAPCs showed significant improvements over the corresponding groups treated with irradiated MAPCs. There was a trend to ward declining recovery over the 56 days of the experiment in the animals treated with 400,000 cells but not those treated with 1,000,000 cells. The same results was obtained with and without immunosuppression.

In sum, animals treated with 1,000,000 viable MAPCs showed a statistically significant, sustained improvement in both locomotor and neurological functioning over the entire 8 week course of the experiment. Tine therapeutic effect, moreover, does not require immunosuppression. The results were the same with and without CSA.

Results are depicted graphically in FIGS. 7 and 8.

Example 13: Effect of Timing on Treatment of Ischemic Stroke in a Rat Surgical Model with Xenogeneic (Human) MAPCs Delivered by I.V. Injection Twenty-Eight SD rats underwent middle cerebral artery MCA ligation surgery to Induce a surgical stroke in the animals. The animals were separated into four cohorts of seven animals each. Each cohort received 1,000,000 xenogeneic (human) MAPCs by intravenous infusion, without immunosuppression. All groups were treated the same except that the MAPCs were administered at different times after induction of stroke. MAPCs were administered to the groups the following number of days after induction: (1) one day, (2) two days, and (3) seven days. In addition group (4) received 1,000,000 irradiated, non-viable MAPCs on day 7 after induction.

No mortality was observed in animals receiving MAPCs during the study.

Example 14: Effect of Timing on Treatment of Ischemic Stroke in a Rat Surgical Model with Xenogeneic (Human) MAPCs Delivered by I.V. Injection—Locomotor and Neurological Function Animals were treated as described in Example 12. At 7 days post cell transplantation, and every 7 days thereafter for 8 weeks, locomotor and neurological function were assessed in each animal by EBST and Bederson tests, respectively.

The results for all three groups of animals treated with viable MAPCs show a eta Helically significant, sustained improvement in both locomotor and neurological function compared to the control group treated with irradiated MAPCs (group 4). There were no statistical differences between the results for locomotor function obtained for the three groups treated with viable MAPCs. The same was true for the results for the three groups for neurological function.

The results demonstrate that MAPCs provide a therapeutic benefit on both locomotor and neurological function when administered by IV on the first to the seventh day following ischemic brain injury.

Results are depicted graphically in FIGS. 9 and 10.

Example 15: Effect of Timing on Treatment of Ischemic Stroke in a Rat Surgical Model with Xenogeneic (Human) MAPCs Delivered by I.V. Injection—Engraftment Animals were treated as described in Example 12. Annuals were sacrificed following the final behavioral tests on day 56 for each group. Brains were harvested from the sacrificed animals. Semi-thin sections of paraffin embedded tissue were prepared from the brains. Sections were stained with DAPI to visualize all cell nuclei and with polyclonal mouse anti-HuNu (human nuclei) antibodies followed by FITC-conjugated goat anti-mouse monoclonal antibodies to stain engrafted human MAPCs. Both the DAPI stained cells and fee FITC stained cells were counted. The total number of engrafted cells was determined from the number of FITC stained cells. The percentage of injected MAPCs that engraft was calculated from fee ratio of fee total number of engrafted cells to fee total number of cells infused into each animal.

The results show somewhat fewer cells engrafted at earlier times of administration after injury. Animals administered with MAPCs one day after injury averaged 0.75% engraftment. Those administered with MAPCs 2 days after injury averaged 1.1% engrafted cells. Animals administered wife MAPCs 7 days after injury averaged 1.27% viable engrafted cells. The trend is not statistically significant; but, it suggests that the inflammatory environment of ischemic injury immediately after a stroke may be less favorable for engraftment and long term survival of MAPCs then the environment present only a few days later.

Example 16: Effect of Timing on Treatment of Ischemic Stroke in a Rat Surgical Model with Xenogeneic (Human) MAPCs Delivered by I.V. Infusion—Neuronal Protection Animals were treated as described in Example 12. Brain sections were prepared as described in Example 14. Alternate sections (to those used in Example 14) were stained with Nissl to determine endogenous neuronal viability. The results show a statistically significant decrease in endogenous neuronal death with MAPC administration. The protective effect of the MAPCs on endogenous neuronal viability increases as the time decreases between stroke induction and MAPC administration. There were more viable neurons in animals receiving MAPCs on day 1 after stroke induction than in those receiving MAPCs on day 2 after stroke induction, and the difference was statistically significant. Similarly, there were more viable neurons in animals receiving MAPCs on day 2 after stroke induction than in those receiving MAPCs on day 7 after stroke induction, and this difference also was statistically significant. The results indicate that the sooner after an Ischemic event MAPCs are administered the greater the protective effect for endogenous neuronal viability.

The results are depicted graphically in FIG. 11.

What is claimed is:

1. A method of ameliorating a brain injury caused by hypoxia in a human subject, comprising: administering to a human subject having a brain injury caused by hypoxia mammalian multipotent adult progenitor cells characterized in that: they are not embryonic stem cells, embryonic germ cells, or germ cells, are allogeneic to the subject, express telomerase, have a normal karyotype, and have undergone at least 10-40 cell doublings in culture, wherein the subject has an immune system and wherein further the subject is not treated with immunosuppressive therapy adjunctively to administration of said cells.

2. A method according to claim 1, wherein said progenitor cells can differentiate into cells of at least two of the endodermal, ectodermal, and mesodermal embryonic lineages.

3. A method according to claim 1, wherein said progenitor cells are human cells.

4. A method according to claim 1, wherein said progenitor cells are derived from cells isolated from any of placental tissue, umbilical cord tissue, umbilical cord blood, bone marrow, blood, spleen tissue, thymus tissue, spinal cord tissue, adipose tissue, and liver tissue.

5. A method according to claim 4, wherein said progenitor cells are derived from bone marrow.

6. A method according to claim 5, wherein said progenitor cells are derived from human bone marrow.

7. A method according to any one of claims 1, 3 6, wherein the brain injury is hypoxic ischemic brain injury.

8. A method according to any one of claims 1, 3 6, wherein the brain injury is caused by an occlusion or a blockage of blood supply.

9. A method according to any one of claims 1, 3 6, wherein the brain injury is a cortical infarction.

10. A method according to any one of claims 1, 3 6, wherein the brain injury is a stroke.

11. A method according to claim 1, wherein said progenitor cells are administered to said subject in one or more doses comprising $10^5$ to $10^8$ of said cells per kilogram of the subject's mass.

12. A method according to claim 11, wherein said progenitor cells are administered to the subject in one or more doses comprising $10^6$ to $5\times10^7$ of said progenitor cells per kilogram of the subject's mass.

13. A method according to claim 1, wherein in addition to said progenitor cells, one or more growth factors, differentiation factors, signaling factors, and/or factors that increase homing are administered to said subject.

14. A method according to claim 1, wherein further any combination of one or more of each of the following is administered to said subject: an antibiotic agent, an anti-fungal agent, and/or an anti-viral agent.

15. A method according to claim 1, wherein said progenitor cells are administered in a formulation comprising one or more other pharmaceutically active agents.

16. A method according to claim 15, wherein said formulation further comprises any combination of one or more of: an antibiotic agent, an anti-fungal agent, and/or an anti-viral agent.

17. A method according to claim 1, wherein said progenitor cells are administered to the subject by a parenteral route.

18. A method according to claim 17, wherein said progenitor cells are administered by intravenous infusion.

19. A method according to claim 1, wherein said progenitor cells are administered to the subject by stereotactic injection.

20. A method according to claim 2, wherein said progenitor cells are derived from human bone marrow.

21. A method according to claim 20, wherein the brain injury is hypoxic ischemic brain injury.

22. A method according to claim 20, wherein the brain injury is caused by an occlusion or a blockage of the blood supply.

23. A method according to claim 20, wherein the brain injury is a cortical infarction.

24. A method according to claim 20, wherein the brain injury is a stroke.

* * * * *